(12) United States Patent
Yamaguchi

(10) Patent No.: US 10,975,346 B2
(45) Date of Patent: *Apr. 13, 2021

(54) PROCESS FOR PRODUCING NOVEL SIALO-SUGAR CHAIN

(71) Applicant: WAKAYAMA UNIVERSITY, Wakayama (JP)

(72) Inventor: Masanori Yamaguchi, Wakayama (JP)

(73) Assignee: WAKAYAMA UNIVERSITY, Wakayama (JP)

( * ) Notice: Subject to any disclaimer, the term of this patent is extended or adjusted under 35 U.S.C. 154(b) by 169 days.

This patent is subject to a terminal disclaimer.

(21) Appl. No.: 15/041,396

(22) Filed: Feb. 11, 2016

(65) Prior Publication Data

US 2016/0160163 A1 Jun. 9, 2016

Related U.S. Application Data

(62) Division of application No. 14/345,772, filed as application No. PCT/JP2012/073181 on Sep. 11, 2012, now Pat. No. 9,290,532.

(30) Foreign Application Priority Data

Sep. 20, 2011 (JP) ............................. JP2011-204579
Dec. 28, 2011 (JP) ............................. JP2011-287308

(51) Int. Cl.
| | |
|---|---|
| *C12M 1/40* | (2006.01) |
| *C07H 15/26* | (2006.01) |
| *C12P 19/26* | (2006.01) |
| *C07H 13/04* | (2006.01) |
| *C07H 15/10* | (2006.01) |
| *C07H 17/02* | (2006.01) |
| *C12M 1/00* | (2006.01) |

(52) U.S. Cl.
CPC ............ *C12M 21/18* (2013.01); *C07H 13/04* (2013.01); *C07H 15/10* (2013.01); *C07H 15/26* (2013.01); *C07H 17/02* (2013.01); *C12M 47/12* (2013.01); *C12P 19/26* (2013.01)

(58) Field of Classification Search
CPC .......... C07H 13/04; C07H 5/10; C07H 15/26; C07H 7/02; C12M 21/18; C12M 47/12; C12P 19/26

See application file for complete search history.

(56) References Cited

U.S. PATENT DOCUMENTS 5,500,342 A 3/1996 Miyamura et al.

FOREIGN PATENT DOCUMENTS

| JP | 3-262495 | 11/1991 |
|---|---|---|
| JP | 7-112996 | 5/1995 |
| JP | 8-336395 | 12/1996 |
| JP | 2000-502565 | 3/2000 |
| JP | 2005-500058 | 1/2005 |
| JP | 2006-519878 | 8/2006 |
| JP | 2008-526864 | 7/2008 |
| JP | 2008-534665 | 8/2008 |
| WO | 97/23637 | 7/1997 |
| WO | 03/016469 | 2/2003 |
| WO | 2004/080960 | 9/2004 |
| WO | 2006/074279 | 7/2006 |
| WO | 2006/106348 | 10/2006 |
| WO | 2009/000803 | 12/2008 |

OTHER PUBLICATIONS

Tanaka et al., A system for Sialic Acid Transfer by Colomic Acid and a Sialidase that Preferentially Hydrolyzes Sialyl alpha-2,8 Linkages, Biosci. Biotech. Biochem., 59 (4), 638-643, 1995.*

Mao et al., Separation of Selected Basic Pharmaceuticals by Reversed-Phase and Ion-Exchange Chromatography Using Thermally Tuned Tandem Columns, Anal. Chem. 2001, 73, 4478-4485.*

Thiem et al., Chemoenzymatic Syntheses of Sialoyloligosaccharides with Immobilized Sialidase, Angew. Chem. Int. Ed. Engl. 30 (1991) No. 11.*

Notification of Reasons for Refusal dated Nov. 22, 2016 in corresponding Japanese Application No. 2013-534668, with English translation.

International Search Report dated Nov. 6, 2012 in International (PCT) Application No. PCT/JP2012/073181.

Kasteren et al., "Expanding the diversity of chemical protein modification allows post-translational mimicry", Nature, vol. 446, No. 7139, Apr. 26, 2007, pp. 1105-1109.

Bay et al., "Induction of a Melanoma-Specific Antibody Response by a Monovalent, but not a Divalent, Synthetic GM2 Neoglycopeptide", ChemMedChem, vol. 4, No. 4, 2009, pp. 582-587.

Fort et al., "Biosynthesis of conjugatable saccharidic moieties of GM2 and GM3 gangliosides by engineered *E. coli*", Chemical Communications, No. 20, 2005, pp. 2558-2560.

Pukin et al., "GM3, GM2 and GM1 mimics designed for biosensing: chemoenzymatic synthesis, target affinities and 900 MHz NMR analysis", Carbohydrate Research, vol. 343, No. 4, 2008, pp. 636-650.

Cao et al., "Parallel chemoenzymatic synthesis of sialosides containing a C5-diversified sialic acid", Bioorganic & Medicinal Chemistry Letters, vol. 19, No. 20, 2009, pp. 5869-5871.

Ajisaka et al., "Regioselective transglycosylation in the synthesis of oligosaccharides: comparison of β-galactosidases and sialidases of various origins", Carbohydrate Research, vol. 259, No. 1, 1994, pp. 103-115.

(Continued)

*Primary Examiner* — Susan M Hanley
(74) *Attorney, Agent, or Firm* — Wenderoth, Lind & Ponack, L.L.P.

(57) ABSTRACT

The present invention provides a novel sialo-sugar chain, a process for producing the sialo-sugar chain, and a device for producing the sialo-sugar chain. A sialo-sugar chain can be easily and efficiently mass-produced by reacting a sugar wherein a hydroxy groups is substituted with an alkynyl group (herein sometimes referred to as "alkynylated sugar") with a specific sialic acid donor in the presence of a sialic acid-introducing enzyme.

4 Claims, 4 Drawing Sheets

(56) References Cited

OTHER PUBLICATIONS

Schmidt et al., "Chemoenzymatic Synthesis of Sialyl Oligosaccharides with Sialidases Employing Transglycosylation Methodology", Journal of Organic Chemistry, vol. 65, No. 25, 2000, pp. 8518-8526.
Thiem et al., "Chemoenzymatische Synthesen von Sialylogosacchariden mit immobilisierter Sialidase", Angewandte Chemie, vol. 103, No. 11, 1991, pp. 1521-1523.
Maru et al., "Synthesis of Sialyllactose from N-Acetylneuraminic Acid and Lactose by a Neuraminidase from *Arthrobacter ureafaciens*", Bioscience, Biotechnology, and Biochemistry, vol. 56, No. 10, 1992, pp. 1557-1561.
Partial Supplementary European Search Report dated Feb. 20, 2015 in European Application No. 12834114.6.
Muthana et al., "Chemoenzymatic Synthesis of a New Class of Macrocyclic Oligosaccharides", J. Org. Chem., vol. 74, No. 8, Mar. 18, 2009, pp. 2928-2936.
Yamaguchi et al., "Developement of efficient construction method of sialo-glycoconjugates toward medicinal applications", Department of Organic Chemistry, Faculty of Education, Wakayama University, Poster 3P-0499 in Event hall, Sep. 23, 2011.
Extended European Search Report dated May 27, 2015 in corresponding European Application No. 12834114.6.
Muthana, J. Am. Chem. Soc. 2007, 129, 11918-11919.
Lu, Tetrahedron 66 (2010) 750-757.
Nishiguchi, Chem. Commun., 2001, 1944-1945.

\* cited by examiner

Device 1a

Device 2a

PROCESS FOR PRODUCING NOVEL SIALO-SUGAR CHAIN

TECHNICAL FIELD

The present invention relates to a novel sialo-sugar chain, a process for producing the sialo-sugar chain, and a device for producing the sialo-sugar chain.

BACKGROUND ART

"Sialo-sugar chain" is a generic term for sugar chains having a sialic acid at the non-reducing end. Sialo-sugar chains are an important constituent of glycolipids, gangliosides, and various glycoprotein sugar chains. Sialo-sugar chains have various functions, such as control of essential phenomena in vital activities such as intercellular recognition, differentiation, and proliferation, as well as association with canceration, virus infection, etc. For example, it has been elucidated that many sialo-sugar chains are present in cancer-related carbohydrate antigens. It has also been elucidated that infection with an influenza virus occurs when a sialylgalactose moiety (a disaccharide consisting of sialic acid and galactose bonded together) expressed on the host cell surface serves as a scaffold.

Sialo-sugar chains, which are involved in such various phenomena, are applicable in a wide variety of fields. Therefore, there is a need to develop a sialo-sugar chain having a structure that can be utilized in many fields.

Furthermore, methods for production or purification of sialo-sugar chains are usually complicated. Therefore, in the production or purification of sialo-sugar chains, extremely high levels of skill, expensive equipment and reagents, and harmful reagents are required. Therefore, there is a need to develop a method for easily and efficiently mass-producing a sialo-sugar chain.

A method comprising reacting lactose and sialic acid in the presence of *Arthrobacter ureafaciens*-derived neuraminidase is known as an example of producing a sialo-sugar chain (Non-patent Literature (NPL) 1). However, this production example is unsatisfactory in terms of easily and efficiently producing a sialo-sugar chain. One specific disadvantage of this method is the production of a plurality of sialo-sugar chains that are different in the non-reducing end of lactose to which the sialic acid of the sialo-sugar chain bonds. Another disadvantage is that sialo-sugar chains produced according to this production example are those comprising sialic acid and lactose simply bonded together, and they are difficult to apply in many fields.

CITATION LIST

NPL 1: Biosci. Biotech. Biochem., 56 (10), 1557-1561, 1992

SUMMARY OF INVENTION

Technical Problem

An object of the present invention is to provide a novel sialo-sugar chain, a process for producing the sialo-sugar chain, and a device for producing the sialo-sugar chain.

Solution to Problem

The present inventors conducted extensive research to achieve the above object. As a result, the inventors found that when a sugar wherein a hydroxy groups is substituted with an alkynyl group (hereinafter sometimes referred to as "alkynyl-introduced sugar") is reacted with a specific sialic acid donor in the presence of a sialic acid-introducing enzyme, a sialo-sugar chain can be easily and efficiently mass-produced.

The inventors further found that the sialo sugar (hereinafter sometimes referred to as "alkynylated sialo-sugar chain") produced by the above production process can be very easily utilized in many fields.

Further, the inventors found that the sialo-sugar chain can be more easily produced by using a column containing a carrier on which a sialic acid-introducing enzyme is immobilized.

More specifically, the present invention includes the following subject matter.

Item 1. A compound represented by formula (5):

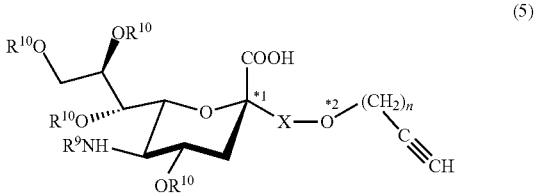

(5)

(wherein X is a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; $R^{10}$ is the same or different, and each represents hydrogen or a hydroxy-protecting group; and n is an integer of 1 to 10).

Item 2. The compound according to Item 1, wherein X in formula (5) is a sugar residue obtained by removing hydroxy from hydroxy at the reducing end of a monosaccharide or an oligosaccharide, and removing hydrogen from hydroxy at a non-reducing end thereof.

Item 3. A compound represented by formula (7a):

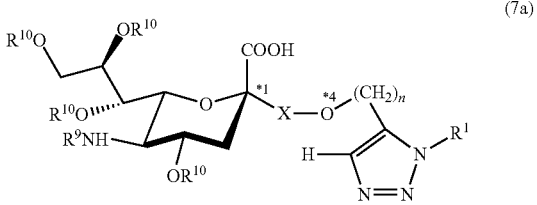

(7a)

(wherein X represents a sugar residue obtained by removing hydroxy from hydroxy at the reducing end of a monosaccharide or an oligosaccharide, and removing hydrogen from hydroxy at the non-reducing end; $R^9$ is hydrogen or a group that acylates an amino group; $R^{10}$ is the same or different, and each represents hydrogen or a hydroxy-protecting group; n is an integer of 1 to 10; and $R^1$ is an organic group), or represented by formula (7b):

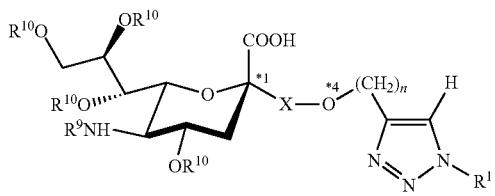

(7b)

(wherein X represents a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; $R^{10}$ is the same or different, and each represents hydrogen or a hydroxy-protecting group; n is an integer of 1 to 10; and $R^1$ is an organic group).

Item 4. A process for producing a compound represented by formula (5):

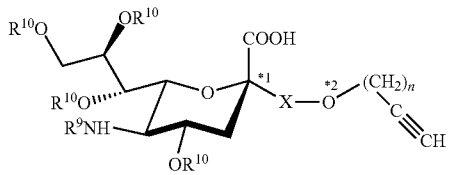

(5)

(wherein X represents a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; and $R^{10}$ is the same or different, and each represents hydrogen or a hydroxy-protecting group; and n is an integer of 1 to 10), the process comprising reacting a sialic acid donor and a compound represented by formula (3):

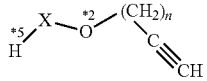

(3)

(wherein X represents a sugar residue obtained by removing hydroxy from hydroxy at the reducing end of a monosaccharide or an oligosaccharide, and removing hydrogen from hydroxy at a non-reducing end thereof; and n is an integer of 1 to 10) in the presence of a sialic acid-introducing enzyme.

Item 5. The process according to Item 4 for producing a compound represented by formula (5):

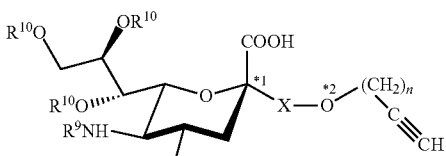

(5)

(wherein X, $R^9$, $R^{10}$, and n are as defined above), the process comprising:

(Step 1) Reacting a Compound Represented by Formula (1):

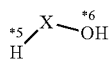

(1)

(wherein X represents a sugar residue obtained by removing hydroxy from hydroxy at the reducing end of a monosaccharide or an oligosaccharide, and removing hydrogen from hydroxy at a non-reducing end thereof) and a compound represented by formula (2):

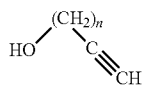

(2)

(wherein n is an integer of 1 to 10)

in the presence of glycosidase to obtain a compound represented by formula (3):

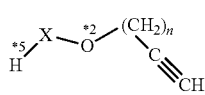

(3)

(wherein X and n are as defined above); and (Step 2) Reacting a Sialic Acid Donor and a Compound Represented by Formula (3):

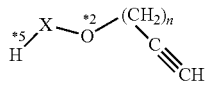

(3)

(wherein X and n are as defined above)

in the presence of a sialic acid-introducing enzyme.

Item 6. The process according to Item 4 or 5, wherein the sialic acid-introducing enzyme is an enzyme immobilized on a carrier.

Item 7. The process according to any one of Items 4 to 6, wherein the sialic acid-introducing enzyme is sialidase, and the sialic acid donor is at least one member selected from the group consisting of compounds represented by formula (4):

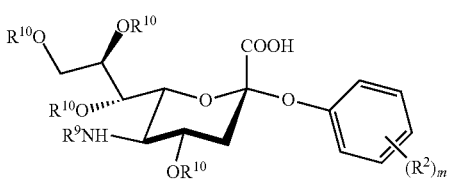

(4)

(wherein $R^2$ is the same or different, and each represents a substituent; $R^9$ is hydrogen or a group that acylates an amino group; $R^{10}$ is the same or different, and each represents hydrogen or a hydroxy-protecting group; and m is an integer of 1 to 3).

Item 8. The process according to Item 7, wherein the sialidase is derived from a microorganism belonging to the genus *Vibrio*.

Item 9. The process according to any one of Items 4 to 6, wherein the sialic acid-introducing enzyme is sialyltransferase, and the sialic acid donor is a compound represented by formula (8):

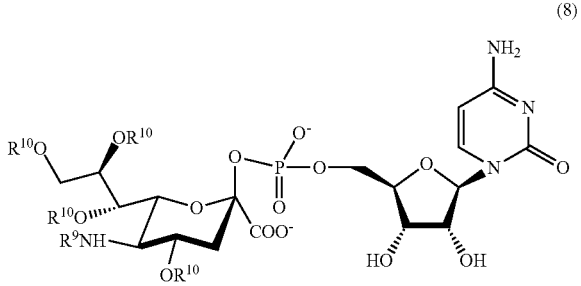

(8)

(wherein $R^9$ is hydrogen or a group that acylates an amino group; and $R^{10}$ is the same or different, and each represents hydrogen or a hydroxy-protecting group).

Item 10. A device comprising a column (hereinafter referred to as "column A") having an inlet and an outlet, and containing glucosidase immobilized on a carrier.

Item 11. The device according to Item 10 comprising
(A) column A and
(B) a reversed-phase column (hereinafter referred to as "column B") having an inlet and an outlet,
wherein the outlet of column A is connected to the inlet of column B via a flow path b, and the flow path b comprises a flow path switching device b'.

Item 12. The device according to Item 10 or 11, which is a device for producing a compound represented by formula (3):

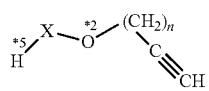

(3)

(wherein X is a sugar residue obtained by removing hydroxy from hydroxy at the reducing end of a monosaccharide or an oligosaccharide, and removing hydrogen from hydroxy at a non-reducing end thereof; and n is an integer of 1 to 10).

Item 13. A device including a column having an inlet and an outlet, the column containing a sialic acid-introducing enzyme immobilized on a carrier.

Item 14. The device according to Item 13, wherein the sialic acid-introducing enzyme is sialidase.

Item 15. The device according to Item 13, wherein the sialic acid-introducing enzyme is sialyltransferase.

Item 16. The device according to Item 13, comprising
(C) a column (hereinafter referred to as "column C") having an inlet and an outlet, and containing a sialic acid-introducing enzyme immobilized on a carrier,
(D) a reversed-phase column (hereinafter referred to as "column D") having an inlet and an outlet, and
(E) an ion-exchange column (hereinafter referred to as "column E") having an inlet and an outlet,
wherein the outlet of column C is connected to the inlet of column D via a flow path d, the outlet of column D is connected to the inlet of column E via a flow path e, the flow path d comprises a flow path switching device d', and the flow path e comprises a flow path switching device e'.

Item 17. The device according to Item 16, wherein the sialic acid-introducing enzyme is sialidase.

Item 18. The device according to Item 16, wherein the sialic acid-introducing enzyme is sialyltransferase.

Item 19. A device comprising the device of Item 10 (hereinafter referred to as "device 1") and the device of any one of Items 13 to 15 (hereinafter referred to as "device 2"), wherein the outlet of device 1 is connected to the inlet of device 2 via a flow path c.

Item 20. A device comprising the device of Item 11 (hereinafter referred to as "device 1a") and the device of any one of Items 16 to 18 (hereinafter referred to as "device 2a"), wherein the outlet of device 1a is connected to the inlet of device 2a via a flow path c.

Item 21. A device according to any one of Items 13 to 20, which is a device for producing a compound represented by formula (5):

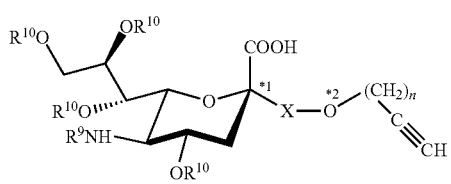

(5)

(wherein X is a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; $R^{10}$ is the same or different, and each represents hydrogen or a hydroxy-protecting group; and n is an integer of 1 to 10).

Item 22. A process for producing a compound represented by formula (3):

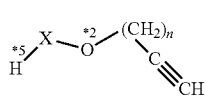

(3)

(wherein X is a sugar residue obtained by removing hydroxy from hydroxy at the reducing end of a monosaccharide or an oligosaccharide, and removing hydrogen from hydroxy at a non-reducing end thereof; and n is an integer of 1 to 10) using the device of Item 10 (hereinafter referred to as "device 1"), the process comprising:

(step a) introducing a compound represented by formula (1):

$$\underset{H}{\overset{*5}{\phantom{|}}}X\overset{*6}{-}OH \qquad (1)$$

(wherein X is a sugar residue obtained by removing hydroxy from hydroxy at the reducing end of a monosaccharide or an oligosaccharide, and removing hydrogen from hydroxy at a non-reducing end thereof) and
a compound represented by formula (2):

$$HO\diagup\overset{(CH_2)_n}{\underset{CH}{\diagdown C}} \qquad (2)$$

(wherein n is an integer of 1 to 10) into column A from the inlet of column A to react the compounds of formulas (1) and (2) to react in column A.

Item 23. The process according to Item 22 for producing a compound represented by formula (3):

$$\underset{H}{\overset{*5}{\phantom{|}}}X\overset{*2}{-}O\diagup\overset{(CH_2)_n}{\underset{CH}{\diagdown C}} \qquad (3)$$

(wherein X and n are as defined above) using the device of Item 11 (device 1a),
the process comprising:

(step a) introducing a compound represented by formula (1):

$$\underset{H}{\overset{*5}{\phantom{|}}}X\overset{*6}{-}OH \qquad (1)$$

(wherein X is as defined above) and
a compound represented by formula (2):

$$HO\diagup\overset{(CH_2)_n}{\underset{CH}{\diagdown C}} \qquad (2)$$

(wherein n is as defined above)
into column A from the inlet of column A to react the compounds of formulas (1) and (2) in column A; and (step b) introducing the reactant in column A into the inlet of column B; and (step c) purifying the compound of formula (3) from column B.

Item 24. A process for producing a compound represented by formula (5):

$$\begin{array}{c}R^{10}O\phantom{xxxx}OR^{10}\\ \phantom{xxxx}COOH\\ R^{10}O\cdots\phantom{xx}O\\ R^9NH\phantom{xx}\overset{*1}{\phantom{|}}X-O\diagup\overset{*2}{\phantom{|}}(CH_2)_n\\ \phantom{xxxxxx}OR^{10}\phantom{xxxxxx}\underset{CH}{\diagdown C}\end{array} \qquad (5)$$

(wherein X is a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; $R^{10}$ is the same or different, and each represents hydrogen or a hydroxy-protecting group; and n is an integer of 1 to 10),
the process comprising:

(step d) introducing a sialic acid donor and a compound represented by formula (3):

$$\underset{H}{\overset{*5}{\phantom{|}}}X\overset{*2}{-}O\diagup\overset{(CH_2)_n}{\underset{CH}{\diagdown C}} \qquad (3)$$

(wherein X is a sugar residue obtained by removing hydroxy from hydroxy at the reducing end of a monosaccharide or an oligosaccharide, and removing hydrogen from hydroxy at a non-reducing end thereof; and n is an integer of 1 to 10) into column C from the inlet of column C.

Item 25. The process for producing a compound represented by formula (5) according to Item 24 using the device of Item 14, wherein the sialic acid donor is at least one member selected from the group consisting of compounds represented by formula (4):

$$\begin{array}{c}R^{10}O\phantom{xxxx}OR^{10}\\ \phantom{xxxx}COOH\\ R^{10}O\cdots\phantom{xx}O\\ R^9NH\phantom{xx}O\phantom{xxx}\\ \phantom{xxxxxx}OR^{10}\phantom{xxxxxx}(R^2)_m\end{array} \qquad (4)$$

(wherein $R^2$ is the same or different, and each is a substituent; $R^9$ is hydrogen or a group that acylates an amino group; $R^{10}$ is the same or different, and each represents hydrogen or a hydroxy-protecting group; and m is an integer of 1 to 3), and colominic acid.

Item 26. The process for producing a compound represented by formula (5) according to Item 24 using the device of Item 15, wherein the sialic acid donor is a compound represented by formula (8):

(8)

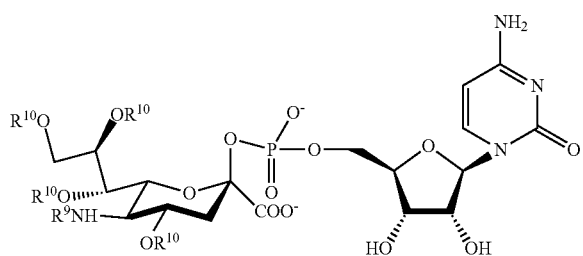

(wherein $R^9$ is hydrogen or a group that acylates an amino group; and $R^{10}$ is the same or different, and each represents hydrogen or a hydroxy-protecting group).

Item 27. The process according to Item 24 for producing a compound represented by formula (5):

(5)

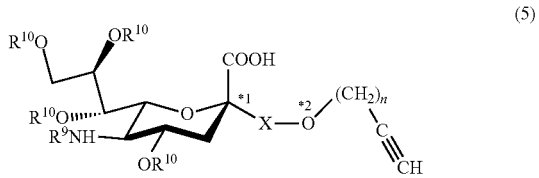

(wherein X, $R^9$, $R^{10}$, and n are as defined above) using the device of Item 16 (hereinafter referred to as "device 2a"), the process comprising:

(step d) introducing a sialic acid donor and a compound represented by formula (3):

(3)

(wherein X and n are as defined above)
into the inlet of column C in device 2;

(step e) introducing the reactant in column C into the inlet of column D;

(step f) introducing the content of column D into the inlet of column E; and (step g) purifying the compound of formula (5) from column E.

Item 28. The process for producing a compound represented by formula (5) according to Item 24 using the device of Item 17, wherein the sialic acid donor is at least one member selected from the group consisting of a compound represented by formula (4):

(4)

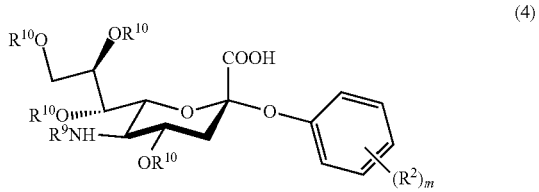

(wherein $R^2$ is the same or different, and each represents a substituent; $R^9$ is hydrogen or a group that acylates an amino group; $R^{10}$ is the same or different, and each represents hydrogen or a hydroxy-protecting group; and m is an integer of 1 to 3) and colominic acid.

Item 29. The process for producing a compound represented by formula (5) according to Item 27 using the device of Item 18, wherein the sialic acid donor is a compound represented by formula (8):

(8)

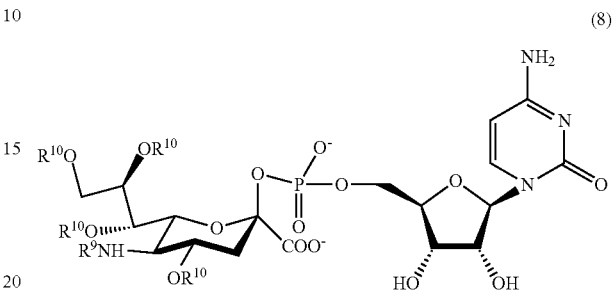

(wherein $R^9$ is hydrogen or a group that acylates an amino group; and $R^{10}$ is the same or different, and each represents hydrogen or a hydroxy-protecting group).

Advantageous Effects of Invention

According to the present invention, a novel sialo-sugar chain, a process for producing the sialo-sugar chain, and a device for producing the sialo-sugar chain can be provided.

The novel sialo-sugar chain of the present invention has a structure in which sugar is substituted with an alkynyl group, as shown in formula (5). Accordingly, the sialo-sugar chain can be linked via the alkynyl group to various materials or probes that can be utilized in various fields, such as the biochemistry and medical fields.

The production process according to the present invention can easily and efficiently mass-produce a sialo-sugar chain without requiring complicated steps, such as protection and deprotection, and without using expensive or hazardous reagents.

Further, by using a column containing a sialic acid-introducing enzyme immobilized on a carrier, a sialo-sugar chain can be more easily produced at a lower cost.

BRIEF DESCRIPTION OF DRAWINGS

FIG. 1 shows a schematic diagram of device 1a.
FIG. 2 shows a schematic diagram of device 2a.
FIG. 3 shows a schematic diagram of device 3a.

DESCRIPTION OF EMBODIMENTS

Figure 1:
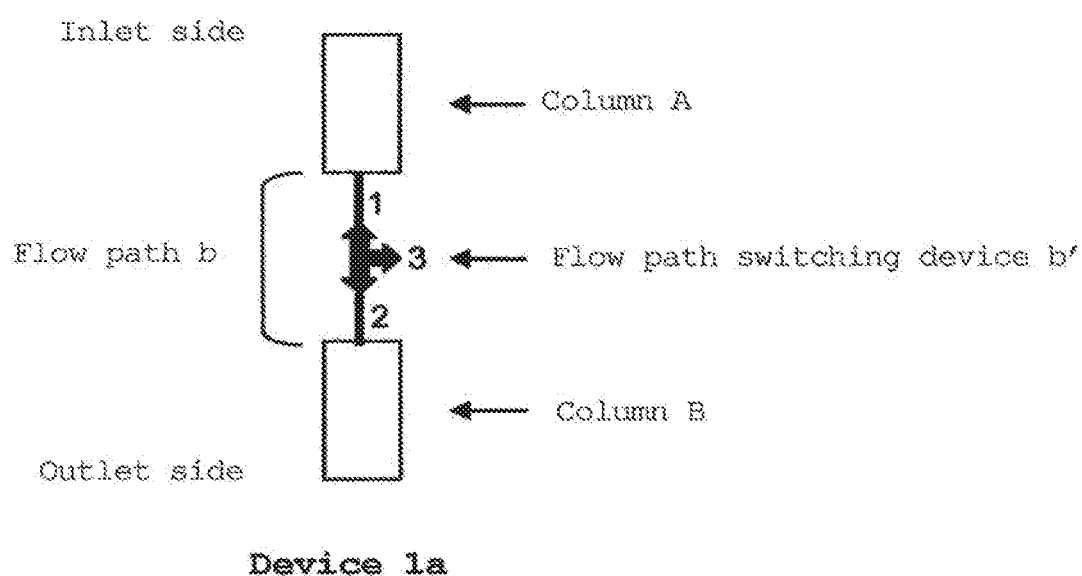

The present invention is described in detail below.

1. Sialo-Sugar Chain, and Sialo-Sugar Chain Linked to an Organic Group

The compound of the present invention is represented by formula (5):

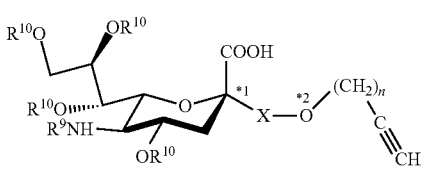

(5)

(wherein X is a sugar residue obtained by removing hydroxy from hydroxy at the reducing end of a monosaccharide or an oligosaccharide, and removing hydrogen from hydroxy at a non-reducing end thereof; $R^9$ is hydrogen or a group that acylates an amino group; $R^{10}$ is the same or different, and each represents hydrogen or a hydroxy-protecting group; and n is an integer of 1 to 10).

X is a sugar residue obtained by removing hydroxy from hydroxy at the reducing end of a monosaccharide or an oligosaccharide, and removing hydrogen from hydroxy at a non-reducing end thereof.

$R^9$ represents hydrogen or a group that acylates an amino group. Specific examples of $R^9$ include hydrogen, acetyl, glycolyl, levulinoyl, chloroacetyl, bromoacetyl, trichloroacetyl, trifluoroacetyl, benzoyl, pivaloyl, troc group, and the like. Among these, acetyl or glycolyl is preferable; and acetyl is more preferable.

$R^{10}$ is the same or different, and each represents hydrogen or a hydroxy-protecting group. Specific examples of $R^{10}$ include hydrogen, a sulfate group, a phosphate group, and the like. Among these, hydrogen or a sulfate group is preferable; and hydrogen is more preferable.

n is an integer of 1 to 10, preferably 1 to 5, more preferably 1 to 3, even more preferably 1 or 2, and particularly preferably 1.

The monosaccharide is not particularly limited, and known monosaccharides can be used. Examples of monosaccharides include heptoses, hexoses, pentoses, tetroses, trioses, and the like. Among these, hexoses are preferable. Examples of hexoses include galactose, glucose, N-acetylglucosamine, N-acetylgalactosamine, mannose, fructose, allose, talose, gulose, altrose, idose, psicose, sorbose, and tagatose. Among these, galactose, glucose, N-acetylglucosamine, and N-acetylgalactosamine are preferable; and galactose or glucose is more preferable. These monosaccharides may be either D or L isomers. Further, monosaccharides may be such that some of hydroxy groups may be reduced and replaced by hydrogen atoms, or some of hydroxy groups may be protected by known protecting groups or substituted with functional groups, such as sulfate groups.

The oligosaccharide is a sugar comprising two or more monosaccharide molecules joined into one molecule through a glycosidic bond. The number of monosaccharide molecules that constitute the oligosaccharide may be, for example, 2 to 20, preferably 2 to 10, more preferably 2 to 5, and even more preferably 2 to 3. The types of monosaccharides constituting the oligosaccharide are not particularly limited; and the monosaccharides mentioned above can be used. There is also no particular limitation on the combination of monosaccharides constituting the oligosaccharide. Specific examples of oligosaccharides include oligosaccharides composed of two monosaccharide molecules (such as lactose, Galβ(1→3)GalNAc, Galβ(1→4)GlcNAc, Galβ(1→6)GlcNAc, sucrose, maltose, trehalose, turanose, and cellobiose), oligosaccharides composed of three monosaccharide molecules (such as raffinose, melezitose, and maltotriose), oligosaccharides composed of four monosaccharide molecules (such as acarbose and stachyose), and oligosaccharides composed of five or more monosaccharide molecules. Among these, oligosaccharides composed of two monosaccharide molecules are preferable. Lactose, Galβ(1→3)GalNAc, Galβ(1→4)GlcNAc, or Galβ(1→6)GlcNAc is more preferable, and lactose is still more preferable.

The sugar residue is a divalent group obtained by removing hydroxy from hydroxy at the reducing end of a monosaccharide or an oligosaccharide, and removing hydrogen from hydroxy at the non-reducing end.

The carbon atom represented by *1 is a carbon atom bonded to the oxygen atom obtained by removing hydrogen from hydroxy at a non-reducing end of X, and the oxygen atom represented by *2 is an oxygen atom bonded to the anomeric carbon atom of X.

The non-reducing end of X from which hydrogen has been removed and which is attached to the carbon atom represented by *1 may be, for example, the 6-position or 3-position, preferably the 6-position.

Specific examples of such sugar residues include sugar residues represented by formula (8a):

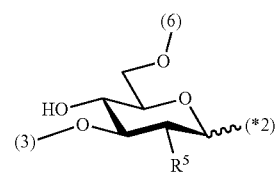

(8a)

(wherein $R^5$ is hydroxy or acetylamino); sugar residues represented by formula (8b):

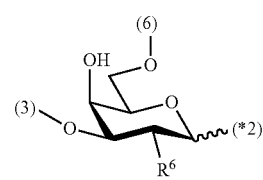

(8b)

(wherein $R^6$ is hydroxy or acetylamino); sugar residues represented by formula (8c):

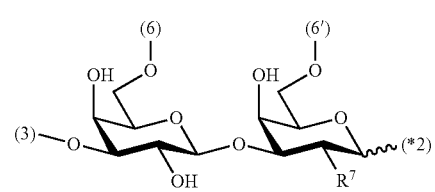

(8c)

(wherein $R^7$ is hydroxy or acetylamino); sugar residues represented by formula (8d):

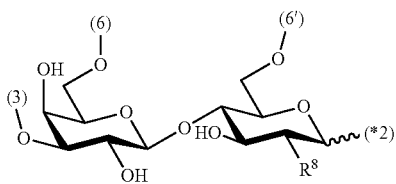

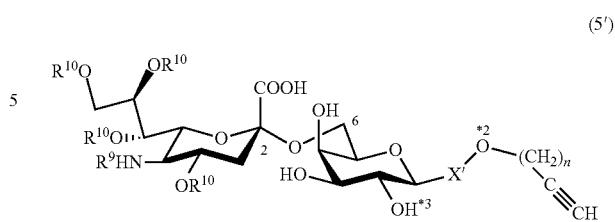

(wherein $R^8$ is hydroxy or acetylamino); and the like.

In formulas (8a) and (8b), (3) and (6) are different, and each represents hydrogen or a bonding site to the carbon atom represented by *1 in formula (5). Preferably, (3) represents hydrogen, and (6) represents a bonding site to the carbon atom represented by *1 in formula (5).

In formula (8c), one of (3), (6), and (6') represents a bonding site to the carbon atom represented by *1 in formula (5), and the other two each represent hydrogen. For example, when (3) represents a bonding site to the carbon atom represented by *1 in formula (5), each of (6) and (6') represents hydrogen. Preferably, each of (3) and (6') represents hydrogen, and (6) represents a bonding site to the carbon atom represented by *1 in formula (5).

In formula (8d), one of (3), (6), and (6') represents a bonding site to the carbon atom represented by *1 in formula (5), and the other two each represent hydrogen. For example, when (3) represents a bonding site to the carbon atom represented by *1 in formula (5), each of (6) and (6') represents hydrogen. Preferably, each of (3) and (6') represents hydrogen, and (6) represents a bonding site to the carbon atom represented by *1 in formula (5).

In formulas (8a), (8b), (8c), and (8d), (*2) represents a bonding site to the carbon atom represented by *2 in formula (5).

An example of the combination of X, $R^9$, $R^{10}$, and n in formula (5) is a combination in which X is lactose, Galβ(1→3)GalNAc, Galβ(1→4)GlcNAc, Galβ(1→6)GlcNAc, galactose, glucose, N-acetylglucosamine, or N-acetylgalactosamine, $R^9$ is acetyl or glycolyl, $R^{10}$ is the same or different, and each represents hydrogen or a sulfate group, and n is 1 to 3. Preferably, X is lactose, galactose, or glucose, $R^9$ is acetyl, $R^{10}$ is hydrogen, and n is 1.

Another example of the combination of X, $R^9$, $R^{10}$, and n in formula (5) is a combination in which X is a sugar residue represented by formula (8a), a sugar residue represented by formula (8b), a sugar residue represented by formula (8c), or a sugar residue represented by formula (8d). In formulas (8a) and (8b), (3) represents hydrogen, and (6) represents a bonding site to the carbon atom represented by *1 in formula (5). In formulas (8c) and (8d), (3) and (6') represent hydrogen, and (6) represents a bonding site to the carbon atom represented by *1 in formula (5). $R^9$ is acetyl or glycolyl, $R^{10}$ is the same or different, and each represents hydrogen or a sulfate group (each $R^{10}$ is preferably hydrogen), and n is 1 to 3.

Another preferable embodiment of the compound of the present invention, i.e., the compound represented by formula (5), is a compound represented by formula (5'):

(wherein X' is a single bond or a group obtained by removing a monosaccharide from X, and $R^9$, $R^{10}$, and n are as defined above).

X' represents a single bond or a group obtained by removing a monosaccharide from X.

The carbon atom represented by *3 is a carbon atom bonded to the oxygen atom obtained by removing hydrogen from hydroxy at the non-reducing end of X.

The compound represented by formula (5') has a structure in which the second carbon of a sialic acid (the carbon represented by "2" in formula (5')) and the sixth carbon of galactose (the carbon represented by "6" in formula (5') are linked via a glycosidic bond, i.e., a Neu5Acα(2→6)Gal structure. Human influenza viruses are known to specifically bind to a sialo-sugar chain having a Neu5Acα(2→6)Gal structure, which is present on the outside of human cell membranes. Accordingly, the compound represented by formula (5'), which has a Neu5Acα(2→6)Gal structure, is excellent in that the compound has the property of specifically binding to a human influenza virus.

The compound represented by formula ( (7a)

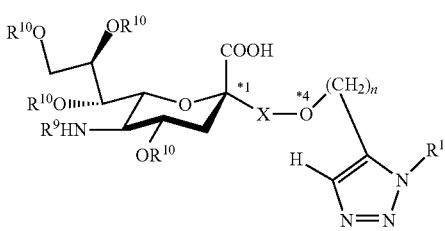

(wherein $R^1$ is an organic group, and X, $R^9$, $R^{10}$, and n are as defined above), and compounds represented by formula (7b):

(7b)

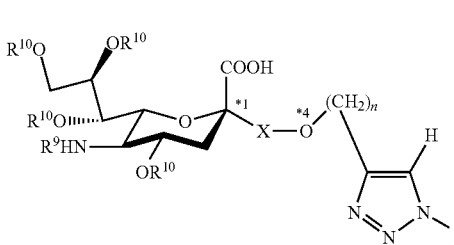

(wherein $R^1$ is an organic group, and X, $R^9$, $R^{10}$, and n are as defined above).

The oxygen atom represented by *4 is an oxygen atom bonded to the anomeric carbon atom of X.

The organic group represented by $R^1$ is not particularly limited, as long as it is a group formed by removing one hydrogen from an organic compound. The organic compound is not particularly limited, as long as the compound has an azido group. Examples of such organic compounds include optionally substituted hydrocarbons, synthetic polymers, natural polymers, and the like.

The optionally substituted hydrocarbon may be linear or branched and may have, for example, 1 to 40 carbon atoms, preferably 5 to 30 carbon atoms, more preferably 8 to 25 carbon atoms, and still more preferably 10 to 20 carbon atoms. Examples of hydrocarbons include saturated hydrocarbons, unsaturated hydrocarbons, chain hydrocarbons, cyclic hydrocarbons, aromatic hydrocarbons, heteroaromatic hydrocarbons, and the like. Examples of substituents include alkyl, vinyl, allyl, aryl, phenyl, naphthyl, araalkyl, benzyl, cycloalkyl, alkoxy, methoxy, ethoxy, and the like.

Examples of synthetic polymers include polyethylene glycol, polyvinyl chloride, phenolic resins, silicone rubber, silicone oil, nylon, vinylon, polyester, polyethylene terephthalate, viscous fibers, copper ammonia fibers, acetate fibers, promix fibers, nylon fibers, vinylon fibers, polyvinylidene chloride synthetic fibers, polyvinyl chloride synthetic fibers, polyester synthetic fibers, polyacrylonitrile synthetic fibers, polyethylene synthetic fibers, polypropylene synthetic fibers, polyurethane synthetic fibers, polychlal synthetic fibers, carbon fibers, and the like.

Examples of natural polymers include proteins, nucleic acids, lipids, sugars, cotton, hemp, linen, silk, hair, and the like. Examples of proteins and nucleic acids include those artificially synthesized by known gene engineering methods. A specific example thereof includes a protein obtained by introducing a foreign DNA into a host cell, and being expressed from the DNA in the host cell.

Specific examples of organic groups represented by $R^1$ are groups represented by formula (9):

$$—C_qH_{2q+1} \qquad (9)$$

(wherein q is an integer of 1 to 40).
The groups represented by formula (9) may be linear or branched.

q is preferably 5 to 30, more preferably 8 to 25, and even more preferably 10 to 20.

Preferable embodiments of formula (9) include groups represented by formula (9a):

$$—(C_2)_r—CH_3 \qquad (9a)$$

(wherein r is an integer of 1 to 39).
r is preferably 4 to 29, more preferably 7 to 24, and more preferably 9 to 19.

Other examples of organic groups represented by $R^1$ include groups represented by formula (10):

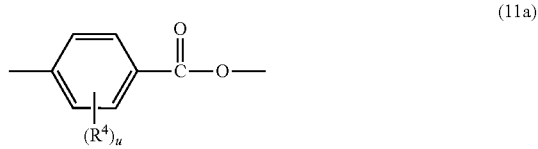

(wherein W is a group represented by formula (11a):

(wherein $R^4$ is a substituent and u is an integer of 1 to 3); and groups represented by formula (11b):

(wherein $R^4$ and u are as defined above); and groups represented by formula (11c):

$$—(CH_2)_v—O— \qquad (11c)$$

(wherein v is an integer of 1 to 8),
s is an integer of 1 to 4, t is an integer of 1 to 30, and $R^3$ is a substituent).

$R^3$ is a substituent, and specific examples thereof include methyl, acetyl, ethyl, allyl, phenyl, benzoyl, benzyl, acyl-based protecting groups, ether-based protecting groups, methacryl, and the like.

$R^4$ is a substituent, and specific examples thereof include methyl, ethyl, alkyl, hydroxy, methoxyl, and ethoxyl.

s is an integer of 1 to 4, and preferably an integer of 2 to 3.

t is an integer of 1 to 30, preferably 4 to 20, and more preferably 8 to 16.

u is an integer of 1 to 3.

v is an integer of 1 to 8, and preferably 1 to 3.

The compounds represented by formula (7a) and (7b) can be used in various fields according to the type of organic group. These compounds can be used, for example, in the biochemistry or medical field, more specifically, for preparation of sugar chain vaccines and monoclonal antibodies; drug delivery systems; TLC/virus binding assays; molecular interaction analysis; air washer filters; masks; etc.

When the organic group is a group obtained by removing one hydrogen from nylon, viscous fibers, copper ammonia fibers, acetate fibers, promix fibers, nylon fibers, vinylon fibers, polyvinylidene chloride synthetic fibers, polyvinyl chloride synthetic fibers, polyester synthetic fibers, polyacrylonitrile synthetic fibers, polyethylene synthetic fibers, polypropylene synthetic fibers, polyurethane synthetic fibers, polychlal synthetic fibers, carbon fibers, cotton, hemp, linen, silk, or wool, or a group that can be used as a fibrous raw material, such as a group represented by formula (10), the compound can be used, for example, in air washer filters, masks, etc., for removal of substances that have the property of binding to a sialo-sugar chain (e.g., viruses such as influenza viruses). Additionally, when the organic group is a group obtained by removing one hydrogen from an appropriate organic compound, an organic group linked to a sialo-sugar chain can be attached to fibers (more specifically, for example, an aqueous solution containing an organic group linked to a sialo-sugar chain can be sprayed over fibers, and then dried) to produce air wash filters, masks, etc., to which a sialo-sugar chain is attached.

When the organic group is a hydrocarbon group as in compounds represented by formula (9), the compound can be used, for example, for preparation of sugar chain vaccines, monoclonal antibodies, etc., by utilizing the immunogenicity enhancement of sialo-sugar chains by the addition of hydrocarbon groups.

The combination of X, $R^9$, $R^{10}$, n, and $R^1$ in formulas (7a) and (7b) may be, for example, a combination in which X is lactose, Galβ(1→3)GalNAc, Galβ(1→4)GlcNAc, Galβ(1→6)GlcNAc, galactose, glucose, N-acetylglucosamine, or N-acetylgalactosamine, $R^9$ is acetyl or glycolyl, $R^{10}$ is the same or different, and each represents hydrogen or a sulfate group, n is 1 to 3, and $R^1$ is a group obtained by removing one hydrogen from hydrocarbon, a synthetic polymer, or a natural polymer. A preferable combination thereof may be a combination in which X is lactose, galactose, or glucose, $R^9$ is acetyl, $R^{10}$ is hydrogen, n is 1, and $R^1$ is a group obtained by removing one hydrogen from nylon, viscous fibers, copper ammonia fibers, acetate fibers, promix fibers, nylon fibers, vinylon fibers, polyvinylidene chloride synthetic fibers, polyvinyl chloride synthetic fibers, polyester synthetic fibers, polyacrylonitrile synthetic fibers, polyethylene synthetic fibers, polypropylene synthetic fibers, polyurethane synthetic fibers, polychlal synthetic fibers, carbon fibers, cotton, hemp, linen, silk, or wool.

2. Sialo-Sugar Chain, and Method for Producing the Sialo-Sugar Chain Linked to an Organic Group The sialo-sugar chain of the present invention and the sialo-sugar chain linked to an organic group can be produced, for example, by steps 1 to 3 shown in the following reaction scheme.

(1)

(1)

(2)

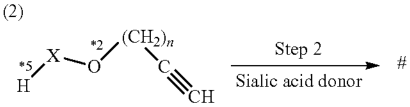

(3)

-continued 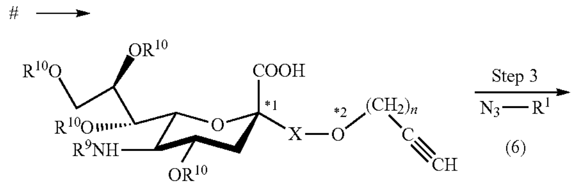 (6)

(5)

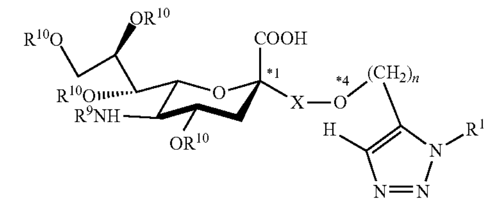

(7a)

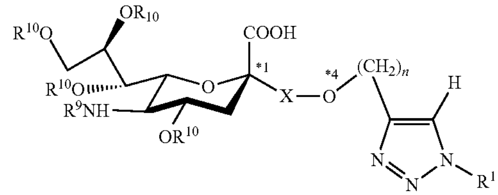

(7b)

(wherein X, n, $R^1$, $R^9$, and $R^{10}$ are as defined above).

Steps 1 to 3 are explained below.

2-1. Step 1 ((1)+(2)→(3))

Step 1 is a process for producing a compound represented by formula (3). The process comprises reacting a compound represented by formula (1) with a compound represented by formula (2) in the presence of glycosidase.

The hydrogen atom designated by *5 is a hydrogen atom bonded to an oxygen atom obtained by removing hydrogen from hydroxy at a non-reducing end of X. The oxygen atom designated by *6 is an oxygen atom bonded to the anomeric carbon atom of X.

There is no particular limitation on the glycosidase. For example, known exoglycosidases and endoglycosidases can be used, and exoglycosidases are preferable. Specific examples of such glycosidases are cellulase, glucosidase, lactase, amylase, chitinase, sucrase, xylanase, maltase, invertase, hyaluronidase, and the like.

The glycosidase to be used is selected according to the type of sugar residue having an anomeric carbon atom bonded to the oxygen atom designated by *6 in the compound represented by formula (1). When X is a monosaccharide residue, an enzyme that recognizes X is selected. For example, when the compound represented by formula (1) has a glucose residue at an end, the sugar residue having an anomeric carbon atom bonded to the oxygen atom designated by *6 is the glucose residue; therefore, a glycosidase that recognizes a glucose residue, such as cellulase or glucosidase, preferably cellulase, is selected. Other specific examples are as follows. When the sugar residue at the reducing end is a galactose residue, galactosidase is selected. When the sugar residue is a mannose residue, mannosidase is selected. When the sugar residue is a xylose residue, xylanase is selected. When the sugar residue is an N-acetylglucosamine residue, N-acetylglucosaminidase is selected. When the sugar residue is an N-acetylgalactosamine residue, N-acetylgalactosaminidase is selected. When the sugar residue is an N-acetyllactosamine residue, cellulase is selected.

When X is an oligosaccharide, all of the sugars other than the sugar at the reducing end are preferably sugars different from the sugar at the reducing end to preclude cleavage at a non-terminal position of the sugar chain by the action of glycosidase on the sugars.

The glycosidase to be used is preferably immobilized on a carrier. The method for immobilizing the glycosidase on a carrier may be a known method. The carrier is not particularly limited, as long as the glycosidase can be immobilized thereon. Examples of usable carriers include carriers having a carboxy group that can be bonded via an amide bond to an amino group contained in glycosidase. For example, glycosidase is immobilized on a carrier by forming an amide bond between an amino group of the glycosidase and an activated ester group of sepharose (carrier) obtained by esterifying a carboxy group with N-hydroxysuccinimide (NHS). Another immobilization method comprises activating a carrier with cyanogen bromide to form an amide bond to the amino group of glycosidase.

The reaction is performed in an appropriate solvent. Any solvent that can dissolve the compounds of formulas (1) and (2), and that does not inactivate glycosidase, can be used. Examples of such solvents include water, acetate buffer, phosphate buffer, citrate buffer, boric acid buffer, tartaric acid buffer, Tris buffer, phosphate-buffered saline, and the like. Acetate buffer is preferable.

The reaction temperature is not particularly limited, as long as the glycosidase is not inactivated at the temperature. The reaction temperature can be suitably selected according to the optimum reaction temperature of the glycosidase. For example, the temperature is preferably 5 to 70° C., preferably 30 to 50° C., and more preferably 34 to 40° C.

The reaction time is not particularly limited, as long as glycosidase activity is fully exhibited. The reaction time may be, for example, 1 to 100 hours, preferably 50 to 80 hours, and more preferably 65 to 75 hours.

The reaction pH is not particularly limited, as long as the activity of glycosidase is fully exhibited. The reaction can be performed, for example, at pH 3 to 10, preferably pH 4 to 6, and more preferably pH 4.5 to 5.5.

There is no particular limitation on the molar ratio of the compound of formula (1) to the compound of formula (2), as long as the reaction catalyzed by glycosidase occurs. For example, the compound of formula (2) may be used in an amount of 0.1 to 100 moles, preferably 1 to 50 moles, more preferably 3 to 30 moles, and even more preferably 5 to 15 moles, per mole of the compound of formula (1).

The above reaction is preferably performed in the presence of glycosidase immobilized on a carrier. In this case, the reaction may be carried out by allowing the compound of formula (1) and the compound of formula (2) to be in contact with the glycosidase immobilized on the carrier in a column, and placing the column under the appropriate temperature conditions.

The amount of glycosidase immobilized on a carrier may be, for example, 0.1 to 10 mg, preferably 0.5 to 3 mg, per mL of the carrier.

After the reaction, the solution containing the compound of formula (3) may be further subjected to a purification step. As purification means, known methods (liquid separation, distillation, chromatography, recrystallization, etc.) can be used.

The compound of formula (3) can be easily and efficiently mass-produced by the above step 1.

The compound of formula (3) thus obtained can be used in step 2 below.

2-2. Step 2 ((3)+Sialic Acid Donor→(5))

Step 2 is a process for producing a compound represented by formula (5). This step comprises reacting the compound of formula (3) and a sialic acid donor in the presence of a sialic acid-introducing enzyme.

The sialic acid-introducing enzyme is an enzyme that can introduce sialic acid into sugar. In other words, it is an enzyme that promotes bonding between sugar and sialic acid. More specifically, it is an enzyme that can bond sialic acid to the non-reducing end of sugar. As the sialic acid-introducing enzyme, for example, a sialidase or sialyltransferase can be used. Sialidases are preferable.

There is no particular limitation on the sialidase to be used. For example, known exosialidases and endosialidases can be used, and exosialidases are preferable. Sialidases derived from various organisms can be used. Examples thereof include sialidases derived from organisms of the genus *Vibrio*, organisms of the genus *Arthrobacter*, or organisms of the genus *Clostridium*. *Sialidases derived from organisms of the genus Vibrio are preferable, and sialidases derived from Vibrio cholerae are more preferable.*

There is no particular limitation on the sialyltransferase to be used. Known sialyltransferases can be used. Preferably, α(2-6) sialyltransferase or α(2-3) sialyltransferase can be used. Examples of usable sialyltransferases include those derived from various organisms, such as cows, chickens, pigs, and mice.

The sialic acid-introducing enzyme is preferably an enzyme immobilized on a carrier. The method for immobilizing a sialic acid-introducing enzyme on a carrier is the same as that mentioned above for immobilizing glycosidase on a carrier.

The sialic acid donor is a compound having a sialic acid skeleton. Examples of sialic acid donors include compounds represented by formula (4):

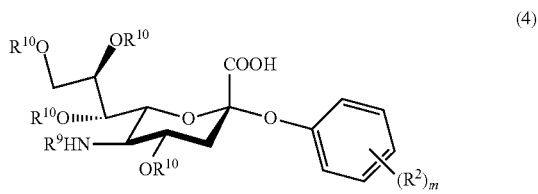

(wherein $R^2$ is the same or different, and each represents a substituent, m is an integer of 1 to 3, and $R^9$ and $R^{10}$ are as defined above), colominic acid, compounds represented by formula (8):

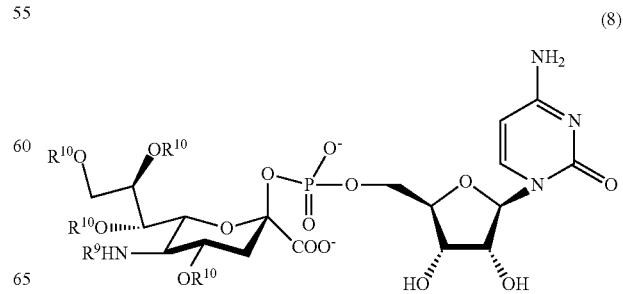

(wherein $R^9$ and $R^{10}$ are as defined above), and compounds represented by formula (12):

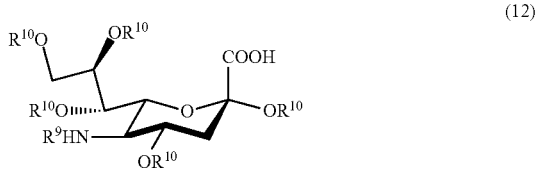
(12)

(wherein $R^9$ and $R^{10}$ are as defined above).

$R^2$ is the same or different, and each represents a substituent. The substituent is not particularly limited, and known substituents can be used. The substituent may be, for example, nitro, fluorine, chlorine, bromine, iodine, hydroxy, alkoxy, or lower alkyl (having 1 to 6 carbon atoms). Nitro, fluorine, chlorine, bromine, or iodine is preferable.

m represents the number of substituted $R^2$, and is an integer of 1 to 3, and preferably 1.

$R^2$ may have a substituent at a para, ortho or meta position, preferably at a para position, relative to the oxygen atom bonded to the benzene ring.

In formula (4), a combination of $R^2$, m, the substitution position of $R^2$, $R^9$, and $R^{10}$ may be, for example, a combination such that $R^2$ is nitro, fluorine, chlorine, bromine, or iodine; m is 1; $R^2$ has a substituent at a para position relative to the oxygen atom bonded to the benzene ring; $R^9$ is acetyl or glycolyl; and $R^{10}$ is the same or different, and each represents hydrogen or a sulfate group. A preferable combination thereof may be, for example, a combination such that $R^2$ is nitro; m is 1; $R^2$ has a substituent at a para position relative to the oxygen atom bonded to the benzene ring; $R^9$ is acetyl; and $R^{10}$ is hydrogen. In formula (8), a combination of $R^9$ and $R^{10}$ may be, for example, such that $R^9$ is acetyl or glycolyl, and $R^{10}$ is the same or different, and each represents hydrogen or a sulfate group. A preferable combination thereof may be, for example, such that $R^9$ is acetyl and $R^{10}$ is hydrogen.

In formula (12), a combination of $R^9$ and $R^{10}$ may be, for example, such that $R^9$ is acetyl or glycolyl, and $R^{10}$ is the same or different, and each represents hydrogen or a sulfate group. A preferable combination thereof may be, for example, such that $R^9$ is acetyl and $R^{10}$ is hydrogen.

Colominic acid is a polymer obtained by polymerizing sialic acid or a salt thereof, and is not particularly limited. Examples of the sialic acid include a wide variety of amino- or hydroxy-substituted neuraminic acid compounds. Specific examples of the sialic acid include N-acetylneuraminic acid, N-glycolylneuraminic acid, and the like. Sialic acid salts are not particularly limited, and examples thereof include sialic acid sodium, sialic acid potassium, and the like. Specific examples of colominic acid salts include colominic acid sodium salt represented by formula:

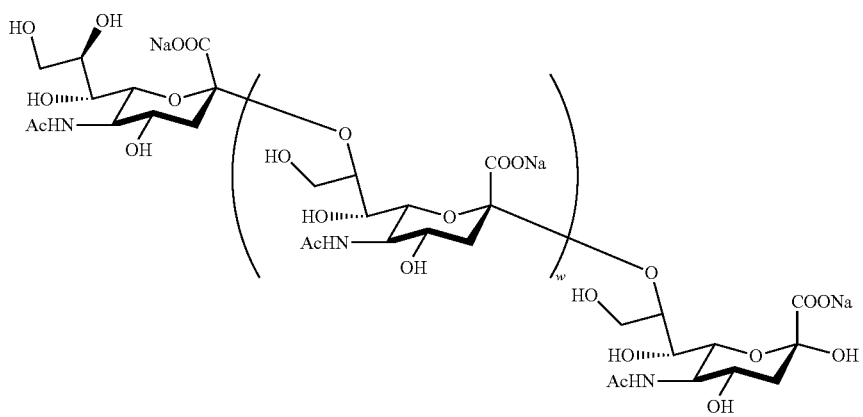
Colominic acid sodium salt (wherein w is 50 to 100).

A preferable combination of the sialic acid-introducing enzyme and the sialic acid donor may be, for example, a combination of sialidase and at least one member selected from the group consisting of compounds represented by formula (4) and colominic acid, or a combination of sialyltransferase and a compound represented by formula (8). A more preferable combination thereof is a combination of sialidase and at least one member selected from compounds represented by formula (4) and colominic acid.

The reaction is performed in an appropriate solvent. The solvent is not particularly limited, as long as it can dissolve the compound of formula (3) and a sialic acid donor, and does not inactivate the sialic acid-introducing enzyme. Usable solvents are the same as in step 1.

The reaction temperature is not particularly limited, as long as the sialic acid-introducing enzyme is not inactivated at the temperature. The reaction temperature can be suitably selected according to the optimum reaction temperature of the sialic acid-introducing enzyme. The temperature may be, for example, 5 to 60° C., preferably 20 to 40° C., and more preferably 27 to 33° C.

The reaction time is not particularly limited, as long as the sialic acid-introducing enzyme is fully exhibited. The reaction time may be, for example, 1 to 48 hours, preferably 12 to 36 hours, and more preferably 20 to 28 hours.

The reaction pH is not particularly limited, as long as the activity of the sialic acid-introducing enzyme is fully exhibited. The reaction can be performed, for example, at pH 3 to 10, preferably pH 4 to 8, and more preferably pH 5 to 6.

The molar ratio of the sialic acid donor to the compound of formula (3) is not particularly limited, as long as the reaction occurs. The molar ratio may be, for example, such that the amount of the sialic acid residue (the group obtained by removing two hydroxy groups from sialic acid) contained in the sialic acid donor is 0.1 to 3 moles, preferably 0.1 to 1 mole, and more preferably 0.15 to 0.25 moles, per mole of the compound of formula (3).

The above reaction is preferably performed in the presence of a sialic acid-introducing enzyme immobilized on a carrier. In this case, the reaction may be carried out by allowing the compound of formula (3) and the sialic acid donor to be in contact with a sialic acid-introducing enzyme immobilized on a carrier in a column, and placing the column under the appropriate temperature conditions. This reaction may be performed by a batch process or a continuous process.

By performing the reaction in the presence of a sialic acid-introducing enzyme immobilized on a carrier, separation of the sialic acid-introducing enzyme after the reaction can be easily performed by removing the carrier by centrifugation, etc.; and the stability of the sialic acid-introducing enzyme is enhanced, allowing the sialic acid-introducing enzyme immobilized on a carrier to be reused. Thus, the compound of formula (5) can be produced more easily and efficiently at lower cost by using a sialic acid-introducing enzyme immobilized on a carrier.

The amount of the sialic acid-introducing enzyme immobilized on a carrier may be, for example, 0.01 to 10 mg, preferably 0.1 to 3 mg, per mL of the carrier.

After the reaction, the solution containing the compound of formula (5) obtained by the reaction may be further subjected to a purification step. Known methods (liquid separation, distillation, chromatography, recrystallization, etc.) can be used as the purification means.

As in step 2 shown above, when a condensation reaction between a sugar and a compound having a sialic acid skeleton is performed in the presence of a sialic acid-introducing enzyme by using the compound of formula (3) as the sugar, the compound of formula (5) can be mass-produced easily and efficiently.

The compound represented by formula (5'), which is encompassed by the compounds of formula (5), can be produced in the same manner as in the production of a compound of formula (5) by using a compound represented by formula (3'):

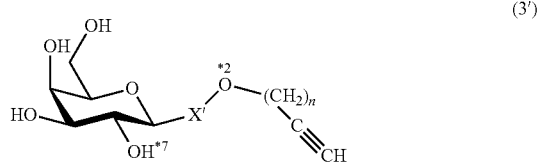

(3')

(wherein X' and n are as defined above) and a sialic acid donor.

By using the compound represented by formula (3'), a compound represented by formula (5') wherein the second carbon of sialic acid (carbon represented by "2" in formula (5')) is linked to the sixth carbon of galactose (carbon represented by "6" in formula (5')) can be efficiently produced.

2-3. Step 3 (5)+(6)→(7a) and (7b))

Step 3 is a process for producing the compounds represented by formulas (7a) and (7b). This step comprises reacting a compound represented by formula (5) and a compound represented by formula (6).

The oxygen atom represented by *4 is an oxygen atom bonded to the anomeric carbon of X.

The compound represented by formula (6) can be produced by a known method.

The reaction is a 1,3-dipole addition reaction. The reaction can be performed in the presence or absence of a solvent. When the reaction is performed in the presence of a solvent, the solvent is not particularly limited, as long as it does not adversely affect the reaction. For example, distilled water, methanol, tetrahydrofuran, dioxane, and/or dimethylsulfoxide can be used. The reaction is preferably performed in the presence of an appropriate catalyst. The catalyst may be, for example, a copper(I) catalyst. When a copper(I) catalyst is used, a method comprising, for example, introducing divalent copper such as copper sulfate and a reducing agent (e.g., sodium ascorbate) into the reaction system and allowing monovalent copper to react may be used.

The reaction temperature is not particularly limited, as long as it is not higher than the boiling point of the solvent. The reaction temperature may be, for example, 15 to 80° C., preferably 20 to 40° C., and more preferably 27 to 33° C.

The reaction time is not particularly limited, and may be, for example, 1 to 24 hours, preferably 6 to 20 hours, and more preferably 10 to 14 hours.

The molar ratio of the compound of formula (5) and the compound of formula (6) in the reaction is not particularly limited. For example, the compound of formula (6) is used in an amount of 1 to 5 moles, preferably 1 to 3 moles, and more preferably 1.25 to 1.75 moles, per mole of the compound of formula (5).

After the reaction, the solution containing the compound of formula (5) obtained by the reaction may be further subjected to a purification step. Known methods (liquid separation, distillation, chromatography, recrystallization, etc.) can be used as the purification means.

3. Production Device

The present invention provides a device 1 (device including a column (hereinbelow referred to as column A) having an inlet and an outlet, and containing glycosidase immobilized on a carrier), a device 2 (device including a column (hereinbelow referred to as column C) having an inlet and an outlet, and containing a sialic acid-introducing enzyme immobilized on a carrier), and a device 3 (including the devices 1 and 2, wherein the outlet of the device 1 is connected to the inlet of the device 2 via a flow path c). The details are explained below.

3-1. Device 1

The device 1 is a device including, as an essential feature, a column (column A) having an inlet and an outlet, and containing glycosidase immobilized on a carrier. Accordingly, the device 1 is suitable for producing the compound represented by formula (3), which is obtained in step 1 above, wherein the reaction is performed in the presence of glycosidase. Namely, the device 1 is preferably a device for producing the compound represented by formula (3).

The inlet side of the column A may include a flow path switching device a' such as a three-way cock or injector.

Further, the device 1 preferably includes a reversed-phase column (hereinbelow referred to as column B) having an inlet and an outlet. The outlet of the column A is preferably connected to the inlet of the column B via a flow path b, and the flow path b preferably includes a flow path switching device b'. The device 1 including the column B and the flow path switching device b' is referred to as a device 1a (FIG. 1).

The flow path switching device b' has a function of switching the direction of the flow path b to any of the three directions, i.e., a column A side (side 1 in FIG. 1), column B side (side 2 in FIG. 1), or external side of the device 1a (side 3 in FIG. 1). Specifically, the flow path switching device b' has a function of closing the flow path at side 3 to connect the flow path at side 1 and the flow path at side 2, a function of closing the flow path at side 2 to connect the flow path at side 1 and the flow path at side 3, and a function of closing the flow path at side 1 to connect the flow path at side 2 and the flow path at side 3.

The outlet side of the flow path b and column B may include various detectors such as an absorbance detector, optical rotation detector, or fluorescence detector, in addition to the flow path switching device b'.

By performing a step (referred to as step a) in which the compound represented by formula (1) and the compound represented by formula (2) are introduced into the column A via the inlet of the column A, and reacted in the column A, using the device 1, a compound represented by formula (3) is produced. In this case, in the column A, the compound represented by formula (1) and the compound represented by formula (2) are reacted in the presence of glycosidase immobilized on a carrier, which is included in the column A, to perform step 1. Accordingly, conditions such as the reaction temperature of step a can be set in the same manner as in step 1 above. The reaction product in the column A, i.e., the reaction product containing the compound represented by formula (3), can be eluted from the column A using a suitable solvent, e.g., a solvent used in the reaction of step (a).

Further, the reaction product containing the compound represented by formula (3) obtained in step a is preferably purified in a column (e.g., column B) connected to the outlet side of the column A. For example, subsequent to step a, purification is preferably performed by a step (hereinbelow referred to as step c) in which the reaction product in the column A is introduced into the inlet of the column B, and a step (hereinbelow referred to as step c) in which the compound represented by formula (3) is purified in the column B.

A method for introducing the reaction product in the column A into the inlet of the column B is not particularly limited, and known methods can be used. For example, a method in which the reaction solution obtained in step (a), which is present in the column A, is extruded from the outlet of the column A by supplying a solvent (preferably, the solvent used in the reaction in step (a)) from the inlet of the column A, and the reaction solution is introduced into the inlet of the column B, which is connected to the outlet of the column A via the flow path b, can be used.

The method of purifying the compound represented by formula (3) from the column B is not particularly limited. A required compound can be purified by changing the kind of a solvent and the mixing ratio according to a known method. For example, by passing through a solvent from the inlet of the column A, or the inlet of the column B, preferably from the external side of the device 1 to the inside of the column B via the flow path switching device b', the compound represented by formula (3) present in the column B is eluted, and a fraction containing the compound is fractionated. The solvent used in this method is not limited as long as the compound represented by formula (3) can be eluted from the column B. For example, water, acetonitrile, methanol, ethanol, and/or tetrahydrofuran can be used.

In this case, unreacted compounds represented by formula (1) and compounds represented by formula (3) are mainly present in the column B. When water is used as a solvent, the unreacted compound represented by formula (1) is eluted first, and then the compound represented by formula (3) is eluted.

The compound represented by formula (3) obtained using the device 1 can be further subjected to a known purification means (e.g., chromatography) and a drying step (e.g., freeze-drying).

Thus, the use of the device 1 ensures an excellent effect, i.e., easy, efficient, and large-scale mass production of the compound represented by formula (3). Specifically, the device 1 is excellent because the use of the column (column A) containing glycosidase immobilized on a carrier is not likely to cause a reduction in glycosidase enzyme activity and enables reuse of the enzyme, and because the use of the column A eliminates the need for enzyme removal after reaction. Further, the device 1 is excellent because the use of the column B remarkably facilitates purification after reaction, and enables reuse of the compound represented by formula (1), which is obtained by the purification in the column B, for the production of the compound represented by formula (3).

3-2. Device 2

The device 2 is a device that includes, as an essential feature, a column (column C) having an inlet and an outlet, and containing a sialic acid-introducing enzyme immobilized on a carrier. Therefore, the device 2 is suitable for the production of the compound represented by formula (5), which is obtained in step (2) above, wherein the reaction is performed in the presence of a sialic acid-introducing enzyme. Namely, the device 2 is preferably a device for producing the compound represented by formula (5).

The inlet side of the column c may include a flow path switching device c', e.g., a three-way cock or injector.

The device 2 preferably includes a reversed-phase column (hereinbelow referred to as column D) having an inlet and an outlet, and/or an ion-exchange column (hereinbelow referred to as column E) having an inlet and an outlet. The outlet of the column C is preferably connected to the inlet of the column D via a flow path d, and the flow path d preferably includes a flow path switching device d'. Further, the outlet of the column D is preferably connected to the inlet of the column E via the flow path e, and the flow path e preferably includes a flow path switching device e'. The device 2 including the column D, column E, flow path switching device d', and flow path switching device e' is referred to as device 2a (FIG. 2).

Figure 2:
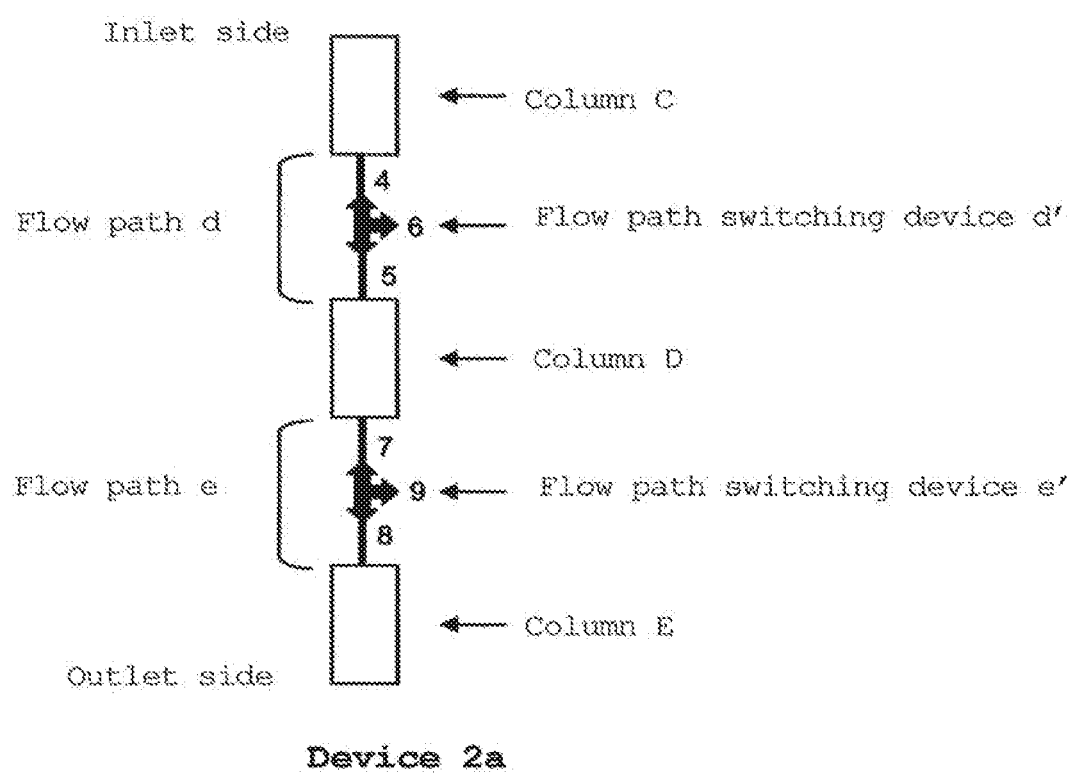

The flow path switching device d' has a function of switching the direction of the flow path d to any of the three directions, i.e., a column C side (side 4 in FIG. 2), column D side (side 5 in FIG. 2), or external side of the device 2a (side 6 in FIG. 2). Specifically, the flow path switching device d' has a function of closing the flow path at side 6 to connect the flow path at side 4 and the flow path at side 5, a function of closing the flow path at side 5 to connect the flow path at side 4 and the flow path at side 6, and a function of closing the flow path at side 4 to connect the flow path at side 5 and the flow path at side 6.

The flow path switching device e' has a function of switching the direction of the flow path e to any of the three directions, i.e., a column D side (side 7 in FIG. 2), column E side (side 8 in FIG. 2), or external side of the device 2a (side 9 in FIG. 2). Specifically, the flow path switching device e' has a function of closing the flow path at side 9 to connect the flow path at side 7 and the flow path at side 8, a function of closing the flow path at side 8 to connect the flow path at side 7 and the flow path at side 9, and a function of closing the flow path at side 7 to connect the flow path at side 8 and the flow path at side 9.

The inlet side of the column C may include the flow path switching device c, e.g., an injector. The outlet side of the flow path d, flow path e, and column E may include various detectors such as an absorbance detector, optical angle detector, or fluorescence detector.

The compound represented by formula (5) can be produced by performing a step (hereinbelow referred to as step d) in which the compound represented by formula (3), and a sialic acid donator are introduced into and reacted in the column C, using the device 2. In this case, in the column C, step 2 is performed by reacting the compound represented by formula (3) and a sialic acid donator in the presence of a sialic acid-introducing enzyme immobilized on a carrier, which is contained in the column C. Therefore, conditions such as the reaction temperature of step d can be set in the same manner as in step 1 above. The reaction product in the column C, i.e., the reaction product containing the compound represented by formula (5), can be eluted from the column C using a suitable solvent, e.g., the solvent used in the reaction of step (d).

Further, the reaction product containing the compound represented by formula (5) obtained in step d is preferably purified in a column (e.g., column D or column E) connected to the outlet side of the column A. For example, subsequent to step d, purification is preferably performed by a step (hereinbelow referred to as step e) in which the reaction product in the column C is introduced in the inlet of the column D, a step (hereinbelow referred to as step f) in which the content in the column D is introduced in the inlet of the column E, and a step (hereinbelow referred to as step g) in which the compound represented by formula (5) is purified in the column E.

A method for introducing the reaction product in the column C into the inlet of the column D is not particularly limited, and known methods can be used. For example, a method in which the reaction solution obtained in step (d), which is present in the column C, is extruded from the outlet of the column C by supplying a solvent (preferably, the solvent used in the reaction in step (d)) from the inlet of the column C, and the reaction solution is introduced into the inlet of the column D, which is connected to the outlet of the column C via the flow path d, can be used.

A method for introducing the reaction product in the column D into the inlet of the column E is not particularly limited, and known methods can be used. For example, a method in which the content obtained in step (d), which is present in the column D, is eluted from the column D by supplying a solvent (e.g., water, acetonitrile, methanol, ethanol, and/or tetrahydrofuran) from the inlet of the column D, and the content is introduced into the inlet of the column E, which is connected to the outlet of the column D via the flow path e, can be used. By performing purification using the column D, unreacted compounds represented by formula (3) and formula (5) can be separated from paranitrophenol generated by the use of the compound represented by formula (4) (paranitrophenol remains in the column D).

The method of purifying the compound represented by formula (5) from the column E is not particularly limited. A required compound can be purified by changing the kind of a solvent and the mixing ratio according to a known method. For example, by passing through a solvent from the inlet of the column C, the inlet of the column D, or the inlet of the column E, preferably from the external side of the device 2 to the inside of the column E via the flow path switching device e', the compound represented by formula (5) present in the column E is eluted, and a fraction containing the compound is fractionated. The solvent used in this method is not limited as long as the compound represented by formula (5) can be eluted from the column E. For example, a sodium chloride aqueous solution, potassium chloride aqueous solution, and/or calcium chloride aqueous solution can be used. When these solvents are used, the concentration of the salt is preferably set to about 0.5 to 2M.

The compound represented by formula (3) in the column E is preferably eluted by introducing water into the column E, and then eluted with a solvent to purify the compound represented by formula (5). The obtained compound represented by formula (3) can be reused for the production of the compound represented by formula (5). The compound represented by formula (5) obtained using the device 1 can be further subjected to a known purification means (chromatography, etc.) and a drying step (freeze-drying, etc.).

Thus, the use of the device 2 ensures an excellent effect, i.e., easy, efficient, and large-scale mass production of the compound represented by formula (5). Specifically, the device 2 is excellent because the use of the column (column C) containing a sialic acid-introducing enzyme immobilized on a carrier is not likely to cause a reduction in enzyme activity of the sialic acid-introducing enzyme and enables reuse of the enzyme, and because the use of the column C eliminates the need for enzyme removal after reaction. Further, the device 2 is excellent because the use of the column D and/or column E remarkably facilitates purification after reaction, and enables reuse of the compound represented by formula (3), which is obtained by the purification in the column E, for the production of the compound represented by formula (3).

3-3. Device 3

As indicated above, the device 3 is a device (hereinbelow referred to as device 3) including the device 1 and the device 2, wherein the outlet of the device 1 is connected to the inlet of the device 2 via the flow path c. Accordingly, the device 3 is suitable for producing the compound represented by formula (5). Namely, the device 3 is a device for producing the compound represented by formula (5).

The outlet of the device 1 means the outlet of the column or device provided at a position closest to the outlet side of the device 1. For example, when the device 1 only includes a column A, the outlet of the device 1 is the outlet of the column A, and when the device 1 is the device 1a including the column A, column B, and the flow path switching device b', the outlet of the device 1 means the outlet of the column B.

The inlet of the device 2 means the inlet of the column provided at a position closest to the inlet side of the device 2, i.e., the inlet of the column C.

The flow path c preferably includes the flow path switching device c', e.g., three-way cock.

The device 3 preferably includes the device 1a and the device 2a.

Figure 3:
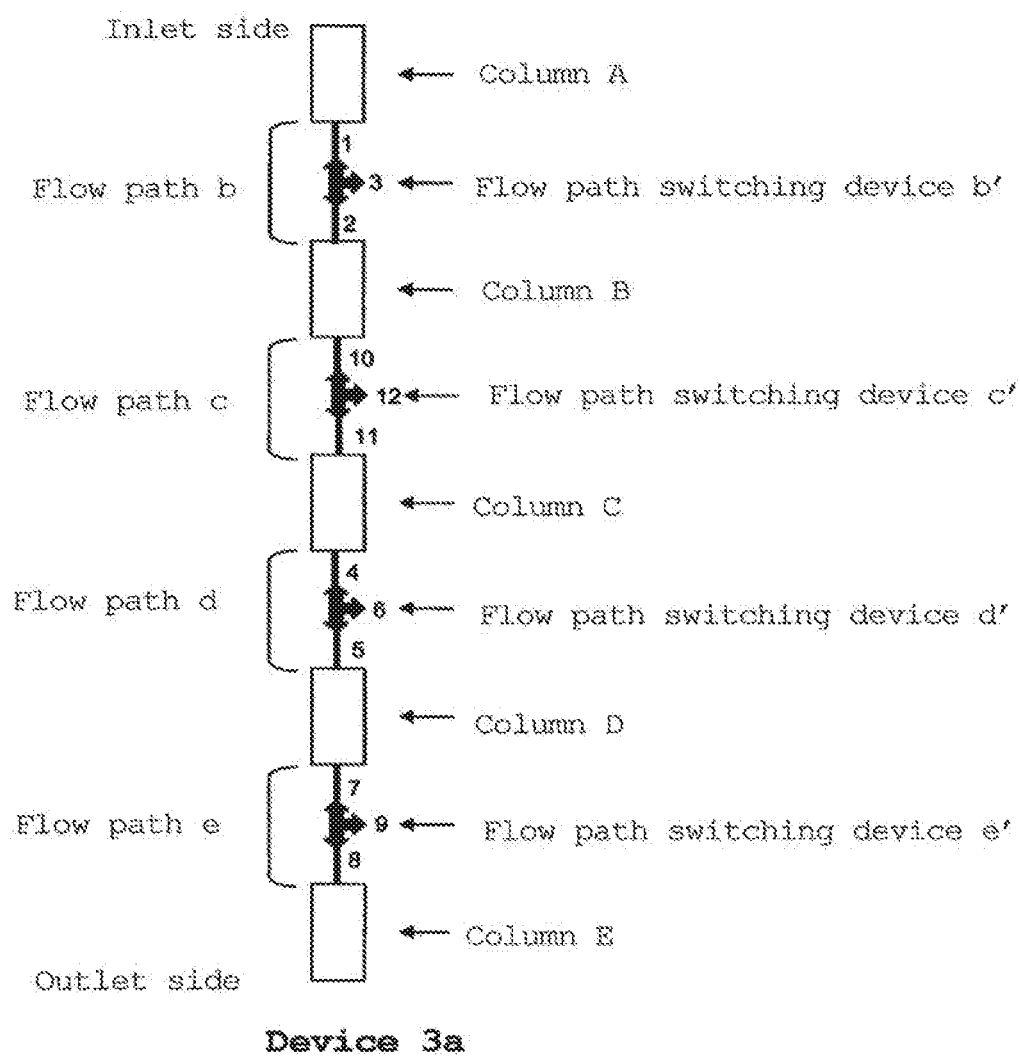

The device 3 including the device 1a, the device 2a, and the flow path switching device c' is referred to as the device 3a (FIG. 3).

The flow path switching device c' has a function of switching the direction of the flow path c to any of the three directions, i.e., a column B side (side 10 in FIG. 3), column C side (side 11 in FIG. 3), or external side of the device 3a (side 12 in FIG. 3). Specifically, the flow path switching device c' has a function of closing the flow path at side 12 to connect the flow path at side 10 and the flow path at side 11, a function of closing the flow path at side 11 to connect the flow path at side 10 and the flow path at side 12, and a function of closing the flow path at side 10 to connect the flow path at side 11 and the flow path at side 12.

The flow path c may include various detectors such as an absorbance detector, optical rotation detector, or fluorescence detector.

By using the device 1 described in the section "3-1. Device 1," the compound represented by formula (3) can be obtained; and by using the device 2 described in the section "3-2. Device 2," the compound represented by formula (5) can be produced. For example, the compound represented by formula (5) can be produced by steps (a) to (g), using the device 3a included in the device 3.

Thus, the use of the device 3 ensures an excellent effect, i.e., easy, efficient, and large-scale mass production of the compound represented by formula (5).

EXAMPLES

The present invention is described in more detail below with reference to Examples. However, the present invention is not limited to these Examples.

Example 1

Preparation of a Column Containing Cellulase Immobilized on a Carrier

Cellulase (produced by Wako Pure Chemical Industries, Ltd., trade name: Cellulase, from *Aspergillus niger*) was immobilized on a carrier in a HiTrap NHS-activated HP column (produced by GE Healthcare Bioscience) by the following steps (1) to (10).
(1) Ice-cooled 1 mM HCl (5 mL) was passed through the column at a flow rate of 0.5 ml/min by using a syringe pump.
(2) 1.8 U (units) of a cellulase solution (cellulase dissolved in a 50 mM sodium acetate buffer (pH=5) (1 mL)) was passed through the column at a flow rate of 0.5 ml/min by using the syringe pump. Subsequently, the column was allowed to stand at 4° C. for 12 hours.
(3) A 0.2 M sodium hydrogencarbonate solution (containing 0.5 M NaCl, pH=8.3) (3 mL) was passed through the column at a flow rate of 0.5 ml/min by using the syringe pump.
(4) A 0.5 M monoethanolamine solution (containing 0.5 M NaCl, pH=8.3) (6 mL) was passed through the column at a flow rate of 1 ml/min by using the syringe pump.
(5) A 0.1 M sodium acetate buffer (containing 0.5 M NaCl, pH=4) (6 mL) was passed through the column at a flow rate of 1 ml/min by using the syringe pump.
(6) A 0.5 M monoethanolamine solution (containing 0.5 M NaCl, pH=8.3) (6 mL) was passed through the column at a flow rate of 1 ml/min by using the syringe pump. Subsequently, the column was allowed to stand at 4° C. for 4 hours.
(7) A 0.1 M sodium acetate buffer (containing 0.5 M NaCl, pH=4) (6 mL) was passed through the column at a flow rate of 1 ml/min by using the syringe pump.
(8) A 0.5 M monoethanolamine solution (containing 0.5 M NaCl, pH=8.3) (6 mL) was passed through the column at a flow rate of 1 ml/min by using the syringe pump.
(9) A 0.1 M sodium acetate buffer (containing 0.5 M NaCl, pH=4) (6 mL) was passed through the column at a flow rate of 1 ml/min by using the syringe pump.
(10) A 50 mM sodium acetate buffer (pH=5) (2 mL) was passed through the column at a flow rate of 1 ml/min by using the syringe pump.

The column obtained by the above steps (1) to (10) was used as a "column containing cellulase immobilized on a carrier" in "Example 3: Production of propargylated lactose" and "Example 7: Production of a device for producing alkynylated sugar."

Example 2

Preparation of a Column Containing Sialidase Immobilized on a Carrier

Sialidase (produced by Roche, *Vibrio cholerae* acylneuraminyl hydrolase) was immobilized on a carrier in a HiTrap NHS-activated HP column (produced by GE Healthcare Bioscience) by the following steps (11) to (20).
(11) Ice-cooled 1 mM HCl (5 mL) was passed through the column at a flow rate of 0.5 ml/min by using a syringe pump.
(12) 1 U (unit) of a sialidase solution (commercially available and adjusted solution) (1 mL) was passed through the column at a flow rate of 0.5 ml/min by using the syringe pump. The column was then allowed to stand at 4° C. for 12 hours.
(13) A 0.2 M sodium hydrogencarbonate solution (containing 0.5 M NaCl, pH=8.3) (3 mL) was passed through the column at a flow rate of 0.5 ml/min by using the syringe pump.
(14) A 0.5 M monoethanolamine solution (containing 0.5 M NaCl, pH=8.3) (6 mL) was passed through the column at a flow rate of 1 ml/min by using the syringe pump.
(15) A 0.1 M sodium acetate buffer (containing 0.5 M NaCl, pH=4) (6 mL) was passed through the column at a flow rate of 1 ml/min by using the syringe pump.
(16) A 0.5 M monoethanolamine solution (containing 0.5 M NaCl, pH=8.3) (6 mL) was passed through the column at a flow rate of 1 ml/min by using the syringe pump. The column was then allowed to stand at 4° C. for 4 hours.
(17) A 0.1 M sodium acetate buffer (containing 0.5 M NaCl, pH=4) (6 mL) was passed through the column at a flow rate of 1 ml/min by using the syringe pump.
(18) A 0.5 M monoethanolamine solution (containing 0.5 M NaCl, pH=8.3) (6 mL) was passed through the column at a flow rate of 1 ml/min by using the syringe pump.
(19) A 0.1 M sodium acetate buffer (containing 0.5 M NaCl, pH=4) (6 mL) was passed through the column at a flow rate of 1 ml/min by using the syringe pump.
(20) A 100 mM sodium acetate buffer (containing 0.5 mM $CaCl_2$, pH=5.5) (2 mL) was passed through the column at a flow rate of 1 ml/min by using the syringe pump.

The column obtained by the above steps (11) to (20) was used as a "column containing sialidase immobilized on a carrier" in "Example 4: Production of propargylated sialyllactose" and "Example 8: Production of a device for producing alkynylated sialo sugar."

Example 3

Production of Propargylated Lactose

Propargylated lactose (compound 3) was produced according to the following reaction scheme. The details are below.

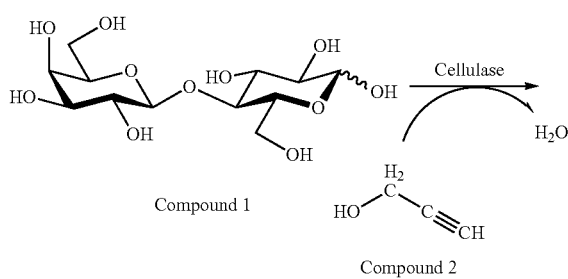

Compound 1

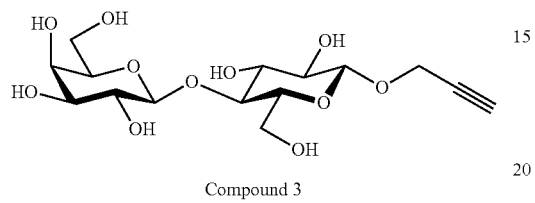

Compound 3

Subsequently, a sodium acetate buffer (50 mM, pH=5.0) (2 mL) was passed through the column to discharge the reaction mixture from the column.

This reaction mixture was supplied to a reversed-phase column (Bondesil-C18, L=6 cm), followed by elution with water. Thereby, compound 3 (49.5 mg) was obtained. The following is the NMR data thereof.

$^1$H-NMR (D$_2$O) δ4.96 (d, 1H, J=3.6 Hz), 4.54 (d, 1H, J=8.4 Hz), 4.34 (s, 2H), 4.32 (d, 1H, J=8.0 Hz), 3.86 (d, 1H, J=11.6 Hz), 3.69-3.52 (m, 4H), 3.42 (dd, 1H, J=8.4, J=9.2 Hz), 3.22 (br-t, 1H), 2.78 (s, 1H).

Example 4

Production of Propargylated Sialyllactose

Propargylated sialyllactose (compound 5) was produced according to the following reaction scheme. The details are below.

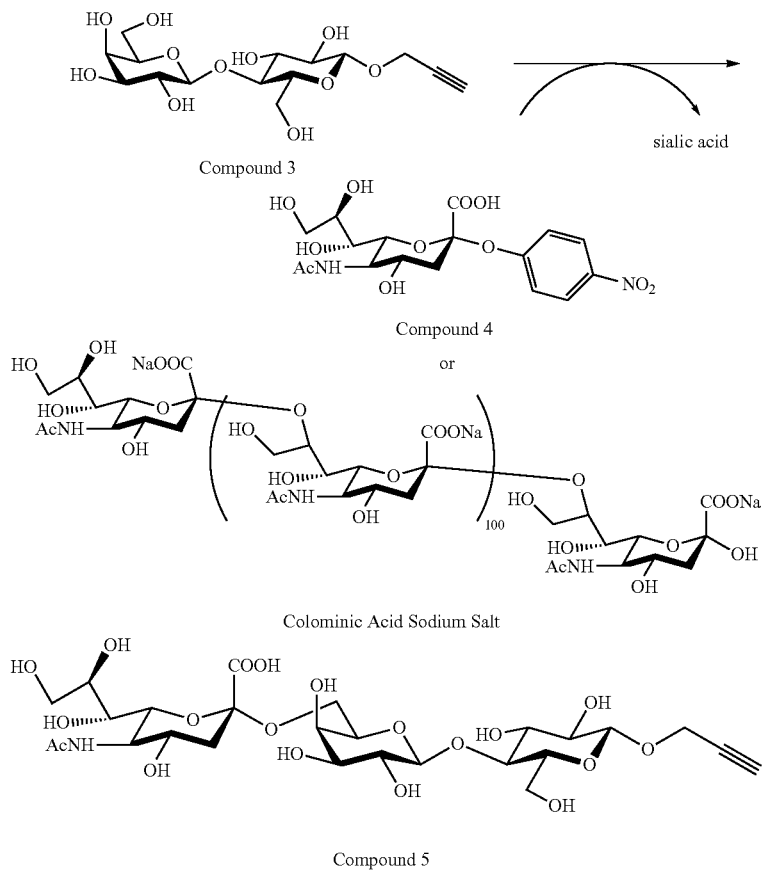

A mixed solution of lactose (compound 1) (1 M, 500 μL), propargyl alcohol (compound 2) (250 μL), and a sodium acetate buffer (50 mM, pH=5.0, 250 μL) was passed through the column produced in Example 1, which contains cellulase immobilized on a carrier.

Both ends of the column were capped, and the column was placed in a thermostatic chamber heated to 37° C., followed by incubation for 70 hours.

Compound 3 (101 mg, 0.26 mmol), and para-nitrophenyl sialic acid prepared according to the Volker Eschenfelder et al. document (Cabohydr. Res. 162, 294-297, 1987) (compound 4) (15.7 mg, 0.05 mmol) or colominic acid (10 mg) (average degree of polymerization: 100) were dissolved in a sodium acetate buffer (100 nM sodium acetate buffer, containing 0.5 mM CaCl$_2$, pH=5.5, 1 mL). The mixed solution was passed through to the immobilized sialidase column.

Both ends of the column were capped, and the column was placed in a thermostatic chamber heated to 30° C., followed by incubation for 24 hours.

Subsequently, a 100 mM sodium acetate buffer (containing 0.5 mM $CaCl_2$, pH=5.5) (2 mL) was passed through the column to discharge the reaction mixture from the column.

This reaction mixture was supplied to a Sep-Pak C18 reversed-phase cartridge column, and unreacted compound 3, the sialic acid, and compound 5 were obtained as a mixture using a water fraction (4 mL) (when colominic acid was used as a donor, this reversed-phase column step was omitted).

The water fraction was then supplied to an ion-exchange cartridge column (AcroSep Q Ceramic Hyper DF). Compound 3 was collected using a water fraction (5 mL), and the sialic acid and the desired compound 5 were obtained as a mixture using a 2 M NaCl fraction (1 mL). The following is the NMR data thereof.

$^1$H-NMR ($D_2O$) δ 4.35 (s, 2H), 4.32 (d, 1H, J=8.0 Hz), 2.68 (d, 1H), 2.50 (dd, 1H, J=4.4, J=12.4 Hz), 1.44 (t, 1H, J=12.4 Hz).

Example 5

Production of Propargylated Sialyllactose in which Polyethylene Glycol is Introduced Propargylated sialyllactose in which polyethylene glycol is introduced (compound 7a) was produced according to the following reaction scheme. The details are below.

According to the K. B. Sharpless et al. document (Angew. Chem. Int. Ed. 41, 2596-2599, 2002), compound 6a (30 μL; 90 μM in DMSO) prepared according to the M. Yamaguchi et al. document (Tetrahedron Lett. 47, 7455-7458, 2006), a 10 mM copper sulfate aqueous solution (50 μL), and a 10 mM sodium ascorbate aqueous solution (50 μL) were added sequentially to an aqueous solution of compound 5 (50 μL) under a nitrogen stream, followed by incubation at 30° C. for 12 hours.

The reaction mixture was concentrated under reduced pressure, and the residue was dissolved in distilled water. The resulting mixture was supplied to a Sep-Pak C18 reversed-phase cartridge column, and sialic acid and unreacted compound 5 were eluted and removed using water (2 mL). Subsequently, an eluate containing the desired compound 7a was obtained using a mixed solvent of water:methanol 1:1 (2 mL) as an elution solvent and concentrated under reduced pressure, thereby obtaining the desired compound 7a. The following is the NMR data thereof.

$^1$H-NMR ($D_2O$) data δ 8.30 (s, 1H), 8.18 (d, 1H), 7.90 (d, 2H, J=8.8 Hz), 7.04 (d, 2H, J=8.8 Hz), 4.31 (m), 3.73 (m), 3.58 (m), 3.49-3.43 (m), 3.18 (s), 2.50 (dd, 1H, J=4.8, J=12.4 Hz), 1.83 (s, 3H), 1.54 (t, 1H, J=12.4 Hz).

Production Example 1

Production of an Azido-Containing Lipid

An azido-containing lipid (compound 6b) was produced according to the following reaction scheme. The details are below.

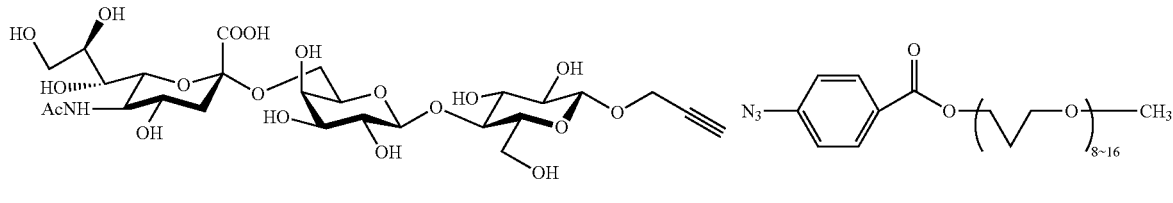

Compound 5　　　　　　　　　　　　　Compound 6a

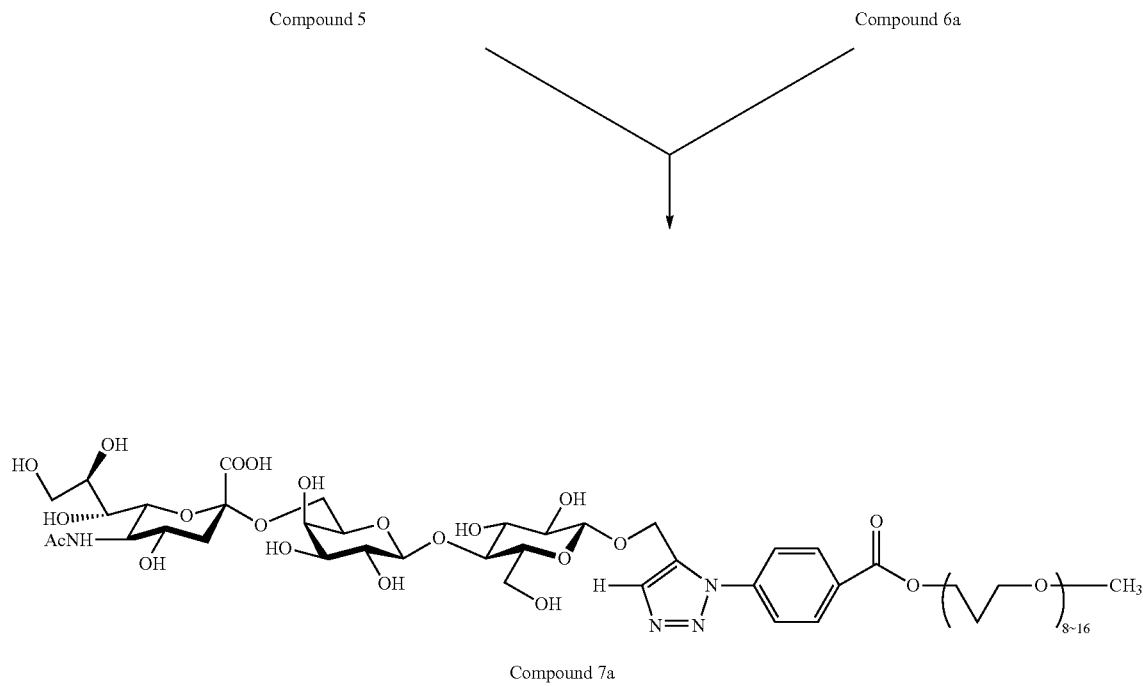

Compound 7a

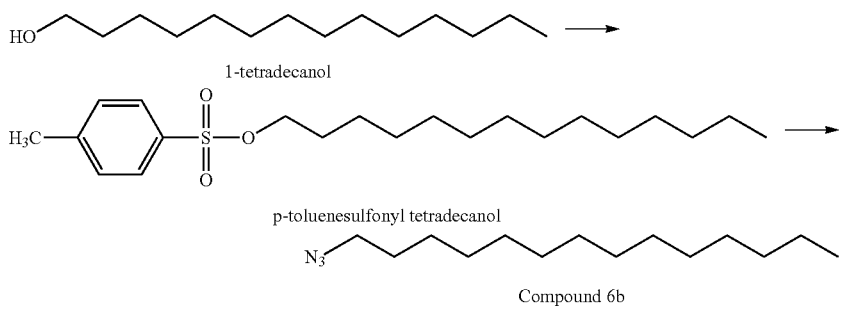

1-tetradecanol (1 g, 4.66 mmol) was dissolved in pyridine (3 mL). p-toluenesulfonyl chloride (1.3 g, 6.82 mmol) was added thereto, and a reaction was carried out with stirring at room temperature for 4 hours.

The reaction mixture was then extracted with chloroform and washed with a 2 M hydrochloric acid aqueous solution. Magnesium sulfate was added thereto, and the resulting mixture was dried and concentrated under reduced pressure.

The obtained syrup was subjected to silica gel column chromatography and purified with an elution solvent (ethyl acetate:hexane=1:10), thereby obtaining p-toluenesulfonyl tetradecanol (1.7 g, yield: 99%).

Subsequently, the obtained p-toluenesulfonyl tetradecanol (1.7 g, 4.61 mmol) was dissolved in N,N-dimethylformamide (3 mL).

Sodium azide (1.4 g, 21.5 mmol) was added thereto at room temperature, and a reaction was carried out with stirring at 40° C. for 24 hours.

The reaction mixture was then extracted with chloroform and washed with distilled water, and magnesium sulfate was added thereto. The resulting mixture was dried and concentrated under reduced pressure.

The obtained syrup was subjected to silica gel column chromatography and purified with an elution solvent (ethyl acetate:hexane=1:10), thereby quantitatively obtaining compound 6b (1.1 g). The following is the NMR data thereof.

$^1$H-NMR (CDCl$_3$) δ3.25 (t), 1.63-1.56 (m), 1.37-1.26 (m), 0.88 (t).

Example 6

Production of Propargylated Sialyllactose in which an Azido-Containing Lipid is Introduced Propargylated sialyllactose in which an azido-containing lipid is introduced (compound 7b) was produced according to the following reaction scheme. The details are below.

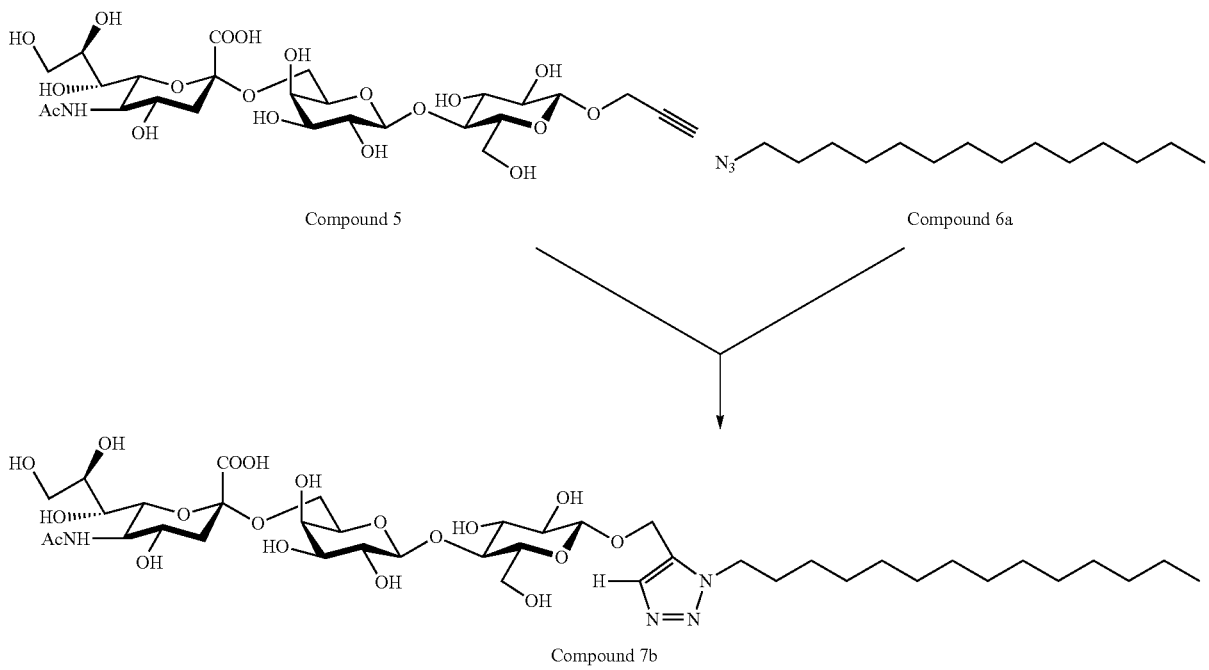

According to the K. B. Sharpless et al. document (Angew. Chem. Int. Ed. 41, 2596-2599, 2002), compound 6b (30 μL; 90 μM in DMSO), a 10 mM copper sulfate aqueous solution (50 μL), and a 10 mM sodium ascorbate aqueous solution (50 μL) were added sequentially to an aqueous solution of compound 5 (50 μL) under a nitrogen stream, followed by incubation at 30° C. for 12 hours.

The reaction mixture was concentrated under reduced pressure, and the residue was dissolved in distilled water. The resulting mixture was supplied to a Sep-Pak C18 reversed-phase cartridge column, and sialic acid and unreacted compound 5 were eluted and removed using water (2 mL). Subsequently, an eluate containing the desired compound 7b was obtained using a mixed solvent of water:methanol=1:1 (2 mL) as an elution solvent and concentrated under reduced pressure, thereby obtaining the desired compound 7b.

$^1$H-NMR (DMSO-D6) δ8.22 (s, 1H), 4.77 (d, 1H, J=5.6 Hz), 4.59 (d, 1H, J=5.2 Hz), 4.22 (t, 1H), 4.16 (d, 1H, J=5.6 Hz), 3.98 (m), 3.66-3.38 (m), 2.18 (dd, 1H, J=4.8, J=12.0 Hz), 1.87 (s, 3H), 1.37 (t, 1H, J=12.0 Hz), 1.01 (m), 0.81 (t, 3H, J=8.8 Hz).

Example 7

Production of Device (1)

A device suitable for the production of a compound that is represented by formula (3) and that is typified by the compound 3 produced in Example 3

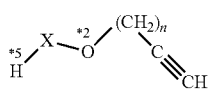

(3)

wherein X and n are as defined above was produced.

The details thereof are described below with reference to FIG. 4, which illustrates the entire device.

A three-way cock a and a three-way cock b were respectively attached to the inlet (upstream) and the outlet (downstream) of the column containing cellulase immobilized on a carrier (immobilized cellulase column A) produced in Example 1.

Further, a reversed-phase column (Bondesil-C18, L=6 cm) (reversed-phase column B) was attached to the downstream side of the three-way cock b.

Example 8

Production of Device (2)

A device suitable for the production of a compound that is represented by formula (5) and that is typified by the compound 5 produced in Example 4

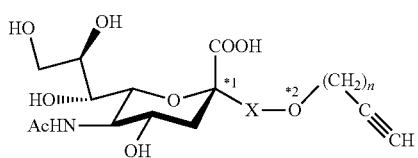

(5)

wherein X and n are as defined above was produced.

The details thereof are described below with reference to FIG. 5, which illustrates the entire device.

A three-way cock c and a three-way cock d were respectively attached to the inlet (upstream) and the outlet (downstream) of the column containing sialidase immobilized on a carrier (immobilized sialidase column C) produced in Example 2.

Two connected reversed-phase cartridge columns (Sep-Pack CIR) (named, from upstream to downstream, as reversed-phase column D1 and reversed-phase column D2) were attached to the downstream side of the three-way cock d (the connected reversed-phase columns D1 and D2 are collectively indicated as reversed-phase column D).

Further, a three-way cock e was attached to the downstream side of the reversed-phase column D2.

Additionally, an ion-exchange cartridge column (AcroSep Q Ceramic Hyper DF) (ion-exchange column E) was attached to the downstream side of the three-way cock e.

Example 9

Figure 4:
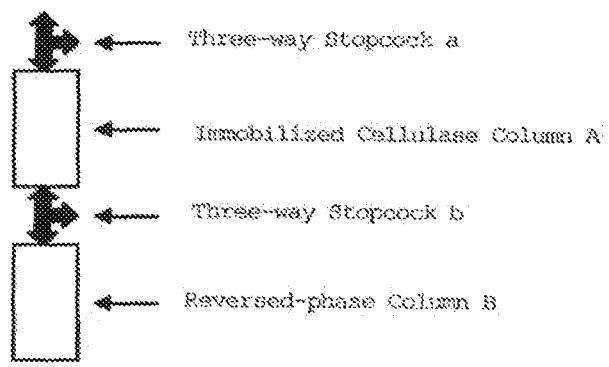
FIG. 4 shows a schematic diagram of the device produced in Example 7 (corresponding to device 1a).

Production of Propargylated Lactose (compound 3) by Using Device 1 for Production of Alkynylated Sugar According to the following reaction scheme, propargylated lactose (compound 3) was produced by using the device produced in Example 7 (FIG. 4). The details thereof are described below.

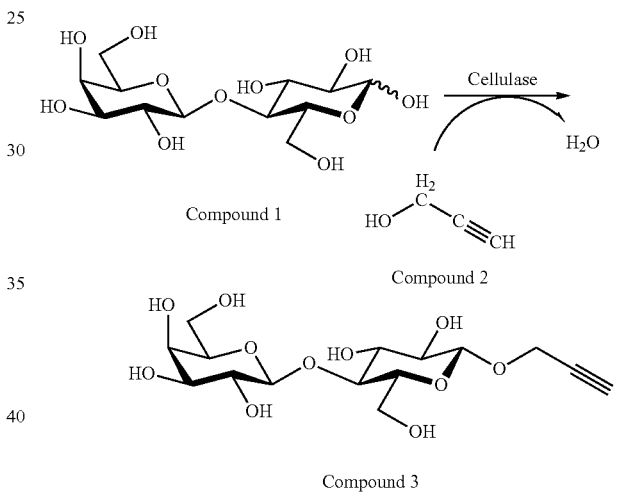

A mixture of an aqueous solution of lactose (compound 1) (1 M, 500 μL), propargyl alcohol (compound 2)(250 μL), and a sodium acetate buffer (50 mM, pH=5.0, 250 μL) was passed through the immobilized cellulase column A via the three-way cock a using a syringe.

At this stage, the flow path of the three-way cock b was directed out of the device to discharge from the device the effluent coming from the outlet of the immobilized cellulase column A without allowing it to pass through the reversed-phase column B via the three-way cock b.

The inlet and outlet of the immobilized cellulase column A were closed, and the immobilized cellulase column A was placed into a thermostatic chamber heated to 37° C., followed by incubation for 70 hours transglucosylation was carried out in the column).

2 mL of a sodium acetate buffer (50 mM, pH: 5.0) was passed through via the three-way cock a. This eluent served to carry the reaction product out of the column, and fill the column with the buffer to stabilize cellulase.

At this stage, the flow path of the three-way cock b was directed to the reversed-phase column B to introduce the eluate drained from the immobilized cellulase column A into the reversed-phase column B.

Distilled water (6 mL) was passed through the reversed-phase column B via the three-way cock b, whereby unreacted lactose (compound 1) and propargylated lactose (compound 3) were separated. Unreacted lactose (compound 1) was eluted with the first half of the distilled water (3 mL). After being concentrated under reduced pressure, this lactose can be recycled for the next reaction. Propargylated lactose (compound 3) was recovered with the latter half of the distilled water (3 mL). The aqueous solution of the compound 3 was concentrated under reduced pressure.

After the desired product is recovered, the reversed-phase column is regenerated for use in the next reaction by sequentially passing a mixture of water and methanol (1:1, 5 ml), methanol (5 mL), and distilled water (5 mL) through the reversed-phase column via the three-way cock.

NMR data: $^1$H-NMR (D$_2$O) δ4.96 (d, 1H, J=3.6 Hz), 4.54 (d, 1H, J=8.4 Hz), 4.34 (s, 2H), 4.32 (d, 1H, J=8.0 Hz), 3.86 (d, 1H, J=11.6 Hz), 3.69-3.52 (m, 4H), 3.42 (dd, 1H, J=8.4, J=9.2 Hz), 3.22 (br-t, 1H), 2.78 (s, 1H)

Example 10

Figure 5:
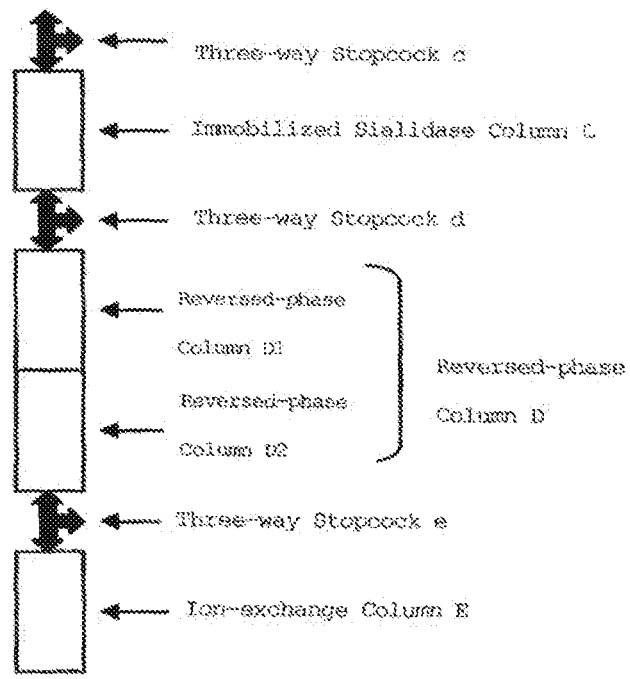
FIG. 5 shows a schematic diagram of the device produced in Example 8 (corresponding to device 2a).

Production of Proparylated Sialyllactose (Compound 5) Using Device 2 for Production of Alkynylated Sialo-Sugar Chain According to the reaction scheme below, propargylated sialyllactose (compound 5) was produced by using the device produced in Example 8 (FIG. 5). The details thereof are described below.

The compound 3 (101 mg, 0.26 mmol), and either para-nitrophenol sialic acid (compound 4) (15.7 mg, 0.05 mmol) or colominic acid sodium salt (10 mg) (average degree of polymerization: 100) represented by the following formula were dissolved in a sodium acetate buffer (100 mM of sodium-acetate buffer, containing 0.5 mM CaCl$_2$, pH=5.5, 1 mL) and passed through the immobilized sialidase column C via the three-way cock c using a syringe. At this stage, the flow path of the three-way cock d was directed out of the device to discharge from the device the effluent coming from the outlet of the immobilized sialidase column C without allowing it to pass through the reversed-phase column D via the three-way cock d.

The inlet and outlet of the immobilized sialidase column C were closed, and the flow path of each of the three-way cocks c and d was turned toward the immobilized sialidase column C. The immobilized sialidase column C was placed into a thermostatic chamber heated to 30° C., followed by incubation for 24 hours (traneglucosylation was carried out in the column).

100 mM of a sodium acetate buffer (containing 0.5 mM CaCl$_2$, pH: 5.5, 2 mL) was passed through via the three-way cock c. This eluent served to carry the reaction product out of the column and fill the column with the buffer to stabilize sialidase. At this stage, the flow path of the three-way cock d was directed to the reversed-phase column D to introduce the eluate drained from the immobilized sialidase column C into the reversed-phase column D.

Distilled water (3 mL) was passed through the reversed-phase column D via the three-way cock d, whereby sugar

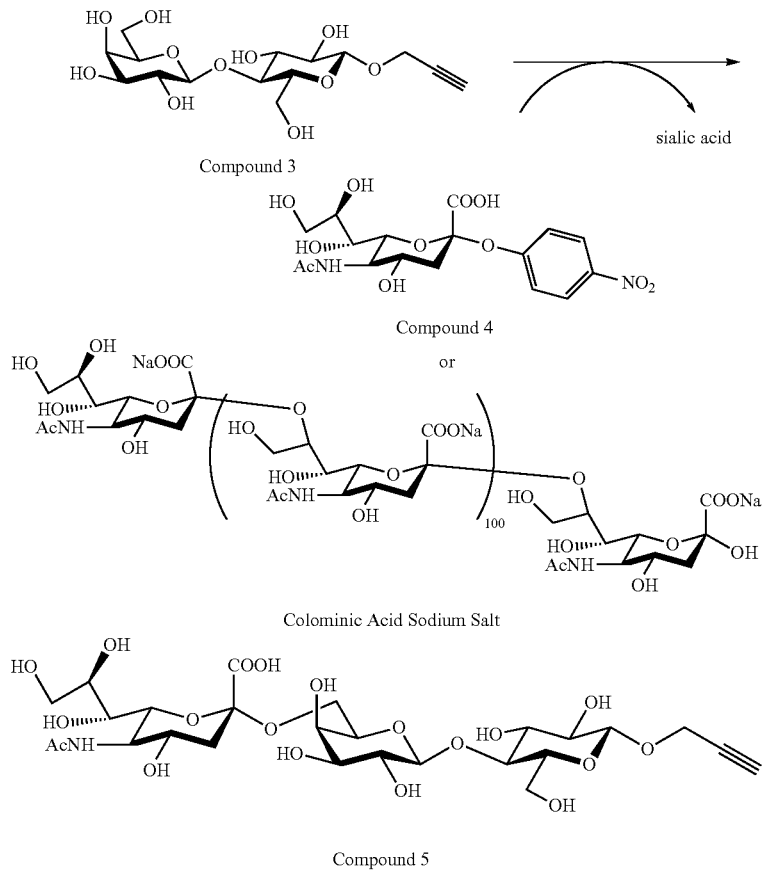

chains were separated from the hydrophobic component (para-nitrophenol that was released during reaction) (*note: the step of the reversed-phase column can be skipped when colominic acid is used as a donor). Sugar chains containing the desired product were completely eluted from the reversed-phase column D with the passed distilled water (3 mL). At this stage, the flow path of the three-way cock e attached to the lower portion of the reversed-phase column was directed to an ion-exchange column E to allow the eluate to flow directly into the subsequently connected ion-exchange column E.

A mixture of water and methanol (1:1, 10 mL), methanol (10 mL), and distilled water (10 mL) were sequentially passed through the reversed-phase column D via the three-way cock d, whereby the reversed-phase column D was regenerated for use in the next reaction. At this stage, the flow path of the three-way cock e was directed out of the device to discharge all of the effluent drained from the reversed-phase column D from the device via the three-way cock e.

Distilled water (5 mL) was passed through the ion-exchange column E via the three-way cock e to thereby recover the compound 3. After being concentrated under reduced pressure, this compound 3 can be recycled in the next reaction. Subsequently, 2 M of a sodium chloride aqueous solution (2 mL) was passed through the ion-exchange column E via the three-way cock e, thereby giving a mixture of propargylated sialyllactose (compound 5) and a free sialic acid.

The ion-exchange column can be regenerated for use in the next reaction by passing distilled water (10 mL) therethrough from the three-way cock e.

NMR data: $^1$H-NMR (D$_2$O) δ4.35 (s, 2H), 4.32 (d, 1H, J=8.0 Hz), 2.68 (d, 1H), 2.50 (dd, 1H, J=4.4, J=12.4 Hz), 1.44 (t, 1H, J=12.4 Hz)

Example 11

Production of Propargylated Sialyllactose (Compound 5) Using Sialyltransferase and CMP-Sialic Acid The procedure described in the above Example was repeated to produce propargylated sialyllactose (compound 5), using sialyltransferase in place of sialidase, and CMP-sialic acid in place of para-nitrophenol sialic acid or colominic acid sodium salt.

The invention claimed is:

1. A device comprising:
(device 1) a device comprising a column A having an inlet and an outlet and comprising glycosidase immobilized on a carrier, a compound represented by formula (1),

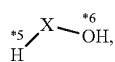

wherein X is a sugar residue obtained by removing a hydroxy from the hydroxy at the reducing end of a monosaccharide or an oligosaccharide, and removing hydrogen from hydroxy at a non-reducing end thereof, a compound represented by formula (2),

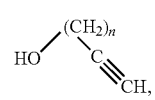

wherein n is an integer of 1 to 10, and
a compound represented by formula (3),

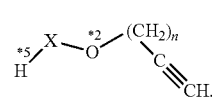

wherein X is a sugar residue obtained by removing a hydroxy from the hydroxy at the reducing end of a monosaccharide or an oligosaccharide, and removing hydrogen from hydroxy at a non-reducing end thereof; and n is an integer of 1 to 10, and
comprising a column B having an inlet and an outlet, and
(device 2) a device comprising a column C having an inlet and an outlet and comprising a sialidase immobilized on a carrier, a sialic acid donor, a compound represented by formula (3),

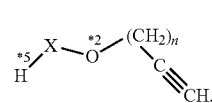

wherein X is a sugar residue obtained by removing a hydroxy from the hydroxy at the reducing end of a monosaccharide or an oligosaccharide, and removing hydrogen from hydroxy at a non-reducing end thereof; and n is an integer of 1 to 10, and
a compound represented by formula (5),

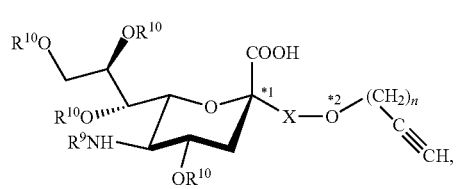

wherein X is a sugar residue obtained by removing a hydroxy from the hydroxy at the reducing end of a monosaccharide or an oligosaccharide, and removing hydrogen from hydroxy at a non-reducing end thereof; $R^9$ is hydrogen, acetyl, glycolyl, levulinoyl, chloroacetyl, bromoacetyl, trichloroacetyl, trifluoroacetyl, benzoyl, pivaloyl, or a troc group; $R^{10}$ is the same or different, and each represents hydrogen or a hydroxy-protecting group; and n is an integer of 1 to 10,
wherein the outlet of column B is connected to the inlet of device 2 via a flow path c.

2. The device according to claim 1, wherein the device 1 comprises:
(A) the column A, and
(B) the column B is a reversed-phase column having an inlet and an outlet, wherein the outlet of the column A is connected to the inlet of the column B via a flow path b, and the flow path b comprises a flow path switching device b'.

3. The device according to claim 1, wherein the device 2 comprises:
   (C) the column C,
   (D) a reversed-phase column D having an inlet and an outlet, and
   (E) an ion-exchange column E having an inlet and an outlet,
   wherein the outlet of the column C is connected to the inlet of the column D via a flow path d, the outlet of the column D is connected to the inlet of the column E via a flow path e, the flow path d comprises a flow path switching device d', and the flow path e comprises a flow path switching device e'.

4. The device according to claim 1, which is a device for producing the compound represented by formula (5).

* * * * *